US010047113B2

(12) United States Patent
Wilkerson et al.

(10) Patent No.: US 10,047,113 B2
(45) Date of Patent: *Aug. 14, 2018

(54) FERULOYL-CoA:MONOLIGNOL TRANSFERASE

(71) Applicants: Wisconsin Alumni Research Foundation (WARF), Madison, WI (US); Board of Trustees of Michigan State University, East Lansing, MI (US); The University of British Columbia, Vancouver (CA)

(72) Inventors: Curtis Wilkerson, Swartz Creek, MI (US); John Ralph, Madison, WI (US); Saunia Withers, Durham, NC (US); Shawn D. Mansfield, Vancouver (CA)

(73) Assignees: Board of Trustees of Michigan State University, East Lansing, MI (US); The University of British Columbia, Vancouver (CA); Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,331

(22) Filed: Aug. 15, 2016

(65) Prior Publication Data

US 2017/0218004 A1 Aug. 3, 2017

Related U.S. Application Data

(63) Continuation of application No. 13/811,823, filed as application No. PCT/US2011/044981 on Jul. 22, 2011, now Pat. No. 9,441,235.

(60) Provisional application No. 61/366,977, filed on Jul. 23, 2010.

(51) Int. Cl.
| | |
|---|---|
| *C12N 15/85* | (2006.01) |
| *C12N 9/10* | (2006.01) |
| *C07G 1/00* | (2011.01) |
| *C08H 7/00* | (2011.01) |
| *C12N 15/82* | (2006.01) |
| *C12P 19/04* | (2006.01) |

(52) U.S. Cl.
CPC ............ *C07G 1/00* (2013.01); *C08H 6/00* (2013.01); *C12N 9/1029* (2013.01); *C12N 15/8255* (2013.01); *C12P 19/04* (2013.01); *C12Y 203/01133* (2013.01)

(58) Field of Classification Search
None
See application file for complete search history.

(56) References Cited

U.S. PATENT DOCUMENTS

| | | | |
|---|---|---|---|
| 4,107,111 A | 8/1978 | Lindberg et al. | |
| 4,478,747 A | 10/1984 | Crawford et al. | |
| 5,451,514 A | 9/1995 | Boudet et al. | |
| 5,824,842 A | 10/1998 | MacKay et al. | |
| 6,287,835 B1 | 9/2001 | Croteau et al. | |
| 6,455,762 B1 | 9/2002 | Chiang et al. | |
| 7,173,164 B2 * | 2/2007 | Brugliera ............ | C12N 9/1025 435/320.1 |
| 7,317,136 B1 | 1/2008 | Forster et al. | |
| 7,413,882 B2 | 8/2008 | Berka et al. | |
| 7,435,556 B2 | 10/2008 | Vitanen et al. | |
| 7,604,968 B2 | 10/2009 | Schmidt-Dannert et al. | |
| 7,981,650 B2 | 7/2011 | Levasseur et al. | |
| 8,569,465 B2 | 10/2013 | Ralph et al. | |
| 9,441,235 B2 * | 9/2016 | Wilkerson ............... | C08H 6/00 |
| 9,487,794 B2 * | 11/2016 | Wilkerson ............... | C08H 6/00 |
| 2001/0007762 A1 | 7/2001 | Echigo et al. | |
| 2003/0070192 A1 | 4/2003 | Keller et al. | |
| 2003/0167511 A1 | 9/2003 | Narbad et al. | |
| 2003/0216326 A1 | 11/2003 | Alimi | |
| 2003/0226168 A1 | 12/2003 | Carlson | |
| 2004/0031072 A1 | 2/2004 | La Rosa | |
| 2004/0049802 A1 | 3/2004 | Dixon et al. | |
| 2004/0058983 A1 | 3/2004 | Vuorela et al. | |
| 2004/0123343 A1 | 6/2004 | La Rosa et al. | |
| 2006/0005270 A1 | 1/2006 | Dunn-Coleman et al. | |
| 2006/0183895 A1 | 8/2006 | Bloksberg et al. | |
| 2008/0032344 A1 | 2/2008 | Fallavollita et al. | |
| 2009/0044294 A1 | 2/2009 | Dixon et al. | |
| 2009/0062516 A1 * | 3/2009 | Belanger ................. | C13K 13/00 530/502 |
| 2009/0087878 A9 | 4/2009 | La Rosa et al. | |
| 2009/0209739 A1 | 8/2009 | Funaoka et al. | |
| 2010/0058498 A1 | 3/2010 | Apuya et al. | |

(Continued)

FOREIGN PATENT DOCUMENTS

| | | |
|---|---|---|
| AU | 2011281001 B2 | 10/2014 |
| AU | 2012318626 B2 | 11/2017 |

(Continued)

OTHER PUBLICATIONS

Wilkerson et al, 2014, Science, 344:90-93.*
"104_164_10434814_5_30003 Sorghum methylation filtered library (LibID: 104) Sorghum bicolor genomic clone 10434814, genomic survey sequence", Retrieved from EBI accession No. EM_GSS:CW024195, Database accession No. CW024195, (May 17, 2010), 1 pg.
"5261_H01_P01Z_001 Brachypodium distachyon callus EST library Brachypodium distachyon cDNA clone 5261_H01_P01, mRNA sequence", Retrieved from EBI accession No. EM_EST:DV471916, Database accession No. DV471916.1, (Oct. 21, 2005), 2 pgs.
"U.S. Appl. No. 12/830,905, Non-Final Office Action dated Jun. 12, 2012", 8 pgs.
"U.S. Appl. No. 12/830,905, Non-Final Office Action dated Dec. 31, 2012", 10 pgs.
"U.S. Appl. No. 12/830,905, Notice of Allowance dated Jun. 13, 2013", 8 pgs.

(Continued)

*Primary Examiner* — Jason Deveau Rosen
(74) *Attorney, Agent, or Firm* — Schwegman Lundberg & Woessner, P.A.

(57) ABSTRACT

The invention relates to nucleic acids encoding a feruloyl-CoA:monolignol transferase and the feruloyl-CoA:monolignol transferase enzyme that enables incorporation of monolignol ferulates, for example, including p-coumaryl ferulate, coniferyl ferulate, and sinapyl ferulate, into the lignin of plants.

32 Claims, 20 Drawing Sheets

(56) References Cited

U.S. PATENT DOCUMENTS

| | | |
|---|---|---|
| 2010/0178670 A1 | 7/2010 | Smith et al. |
| 2010/0287660 A1 | 11/2010 | Spangenberg et al. |
| 2010/0305244 A1 | 12/2010 | Balakshin et al. |
| 2011/0003978 A1 | 1/2011 | Ralph et al. |
| 2013/0203973 A1 | 8/2013 | Wilkerson et al. |
| 2013/0219547 A1 | 8/2013 | Wilkerson et al. |
| 2013/0254930 A1 | 9/2013 | Han et al. |
| 2014/0011984 A1 | 1/2014 | Ralph et al. |
| 2015/0020234 A1 | 1/2015 | Wilkerson et al. |
| 2016/0046955 A1 | 2/2016 | Wilkerson et al. |
| 2017/0096675 A1 | 4/2017 | Wilkerson et al. |

FOREIGN PATENT DOCUMENTS

| | | |
|---|---|---|
| CA | 2806400 C | 9/2017 |
| CL | 201300229 A1 | 1/2013 |
| EP | 2764096 A1 | 8/2014 |
| EP | 2596104 B1 | 11/2016 |
| EP | 2596103 B1 | 12/2016 |
| WO | WO-2012/012698 A1 | 1/2012 |
| WO | WO-2012/012741 A1 | 1/2012 |
| WO | WO-2013/052660 A1 | 4/2013 |
| WO | WO-2013/090814 A2 | 6/2013 |

OTHER PUBLICATIONS

"U.S. Appl. No. 12/830,905, Response filed Apr. 30, 2013 to Non-Final Office Action dated Dec. 31, 2012", 17 pgs.
"U.S. Appl. No. 12/830,905, Response filed Nov. 12, 2012 to Non-Final Office Action dated Jun. 12, 2012", 10 pgs.
"U.S. Appl. No. 13/811,823, Notice of Allowance dated May 6, 2016", 10 pgs.
"U.S. Appl. No. 13/811,823, Preliminary Amendment filed Jan. 23, 2013", 9 pgs.
"U.S. Appl. No. 13/811,823, Supplemental Preliminary Amendment filed Apr. 3, 2013", 3 pgs.
"U.S. Appl. No. 13/811,823, Advisory Action dated Mar. 22, 2016", 4 pgs.
"U.S. Appl. No. 13/811,823, Examiner Interview Summary dated Jan. 26, 2016", 13 pgs.
"U.S. Appl. No. 13/811,823, Examiner Interview Summary dated May 14, 2015", 13 pgs.
"U.S. Appl. No. 13/811,823, Final Office Action dated Nov. 19, 2015", 19 pgs.
"U.S. Appl. No. 13/811,823, Non Final Office Action dated Feb. 27, 2015", 31 pgs.
"U.S. Appl. No. 13/811,823, Response filed Jan. 18, 2016 to Final Office Action dated Nov. 19, 2015", 18 pgs.
"U.S. Appl. No. 13/811,823, Response filed Apr. 19, 2016 to Advisory Action dated Nov. 19, 2015", 16 pgs.
"U.S. Appl. No. 13/811,823, Response filed Jun. 24, 2015 to Non Final Office Action dated Feb. 27, 2015", 19 pgs.
"U.S. Appl. No. 13/811,823, Supplemental Preliminary Amendment filed Jan. 30, 2015", 3 pgs.
"U.S. Appl. No. 13/811,823, Supplemental Preliminary Amendment filed Oct. 13, 2014", 8 pgs.
"U.S. Appl. No. 13/811,823, Supplemental Preliminary Amendment filed Dec. 30, 2014", 9 pgs.
"U.S. Appl. No. 13/811,855, Corrected Notice of Allowance dated May 5, 2016", 6 pgs.
"U.S. Appl. No. 13/811,855, Corrected Notice of Allowance dated Sep. 22, 2016", 2 pgs.
"U.S. Appl. No. 13/811,855, Final Office Action dated Jun. 1, 2015", 7 pgs.
"U.S. Appl. No. 13/811,855, Non Final Office Action dated Jan. 30, 2015", 13 pgs.
"U.S. Appl. No. 13/811,855, Notice of Allowance dated Apr. 19, 2016", 10 pgs.
"U.S. Appl. No. 13/811,855, Notice of Allowance dated May 5, 2016", 6 pgs.
"U.S. Appl. No. 13/811,855, Notice of Allowance dated Jun. 20, 2016", 7 pgs.
"U.S. Appl. No. 13/811,855, Preliminary Amendment filed Jan. 23, 2013", 6 pgs.
"U.S. Appl. No. 13/811,855, Response filed Apr. 30, 2015 to Non Final Office Action dated Jan. 30, 2015", 6 pgs.
"U.S. Appl. No. 13/811,855, Response filed Sep. 1, 2015 to Final Office Action dated Jun. 1, 2015", 6 pgs.
"U.S. Appl. No. 13/811,855, Supplemental Preliminary Amendment filed Apr. 3, 2013", 3 pgs.
"U.S. Appl. No. 14/349,137, Notice of Allowance dated Jun. 29, 2016", 9 pgs.
"U.S. Appl. No. 14/349,137, Response filed May 3, 2016 to Non Final Office Action dated Jan. 4, 2016", 15 pgs.
"U.S. Appl. No. 14/349,137, Non Final Office Action dated Jan. 4, 2016", 20 pgs.
"U.S. Appl. No. 14/349,137, Preliminary Amendment filed Apr. 2, 2014", 7 pgs.
"U.S. Appl. No. 14/349,137, Supplemental Preliminary Amendment filed Aug. 4, 2014", 7 pgs.
"U.S. Appl. No. 14/349,137, Supplemental Preliminary Amendment filed Oct. 6, 2014", 7 pgs.
"U.S. Appl. No. 14/365,744, Preliminary Amendment filed Jun. 16, 2014", 13 pgs.
"U.S. Appl. No. 14/365,744, Preliminary Amendment filed Sep. 10, 2014", 3 pgs.
"U.S. Appl. No. 14/365,744, Supplemental Preliminary Amendment filed Oct. 19, 2015", 4 pgs.
"Australian Serial No. 2011280960, First Examiner Report dated May 23, 2014", 2 pgs.
"Australian Serial No. 2011280960, Response filed Oct. 15, 2014 to First Examiner Report dated May 23, 2014", 4 pgs.
"Australian Serial No. 2011281001, First Examiner Report dated May 23, 2014", 3 pgs.
"Australian Serial No. 2011281001, Response filed Oct. 13, 2014 to First Examiner Report dated May 23, 2014", 22 pgs.
"Brazilian Application Serial No. BR1120130016710, Amendment filed Jul. 22, 2014", (w/ English Translation of Claims), 8 pgs.
"Canadian Application Serial No. 2,851,231, Office Action dated Feb. 8, 2016", 4 pgs.
"Canadian Application Serial No. 2,851,231, Response filed Jul. 27, 2016 to Office Action dated Feb. 8, 2016", 24 pgs.
"Canadian Application Serial No. 2,859,564, Office Action dated Jun. 30, 2015", 4 pgs.
"Canadian Application Serial No. 2,859,564, Response filed Dec. 30, 2015 to Office Action dated Jun. 30, 2015", 21 pgs.
"Chilean Application Serial No. 2013-00229, Office Action dated Jan. 7, 2015", (w/ English Translation), 4 pgs.
"Chilean Application Serial No. 2013-00229, Office Action dated Jul. 3, 2015", (w/ English Translation), 3 pgs.
"Chilean Application Serial No. 2013-00229, Response filed Feb. 24, 2015 to Office Action dated Jan. 7, 2015", with English translation of claims, 9 pgs.
"Chilean Application Serial No. 2013-00229, Response filed Aug. 14, 2015 to Office Action dated Jul. 3, 2015", with English machine translation, 6 pgs.
"European Application Serial No. 11746699.5, Examination Notification Art. 94(3) dated Jun. 8, 2015", 4 pgs.
"European Application Serial No. 11746699.5, Office Action dated Mar. 7, 2013", 2 pgs.
"European Application Serial No. 11746699.5, Office Action dated May 22, 2014", 6 pgs.
"European Application Serial No. 11746699.5, Reply filed Sep. 11, 2013 to Office Action dated Mar. 7, 2013", 19 pgs.
"European Application Serial No. 11746699.5, Response filed Sep. 18, 2014 to Office Action dated May 22, 2014", 11 pgs.
"European Application Serial No. 11746699.5, Response filed Oct. 7, 2015 to Examination Notification Art. 94(3) dated Jun. 8, 2015", 17 pgs.
"European Application Serial No. 11746699.5, Result of Consultation dated Oct. 22, 2014", 3 pgs.
"European Application Serial No. 11746700.1, Examination Notification Art. 94(3) dated May 26, 2014", 5 pgs.

(56) References Cited

OTHER PUBLICATIONS

"European Application Serial No. 11746700.1, Examination Notification Art. 94(3) dated Jun. 12, 2015", 4 pgs.
"European Application Serial No. 11746700.1, Office Action dated Mar. 7, 2013", 2 pgs.
"European Application Serial No. 11746700.1, Reply filed Sep. 11, 2013 to Office Action dated Mar. 7, 2013", 12 pgs.
"European Application Serial No. 11746700.1, Response filed Sep. 18, 2014 to Office Action dated May 26, 2014", 43 pgs.
"European Application Serial No. 11746700.1, Response filed Nov. 10, 2015 to Examination Notification Art. 94(3) dated Jun. 12, 2015", 17 pgs.
"European Application Serial No. 12772693.3, Preliminary Amendment filed Oct. 21, 2014", 9 pgs.
"International Application Serial No. PCT/US2011/044981, International Preliminary Report on Patentability dated Jan. 31, 2013", 10 pgs.
"International Application Serial No. PCT/US2011/044981, International Search Report dated Nov. 3, 2011", 4 pgs.
"International Application Serial No. PCT/US2011/044981, Written Opinion dated Nov. 3, 2011", 10 pgs.
"International Application Serial No. PCT/US2011/045044, International Preliminary Report on Patentability dated Jan. 31, 2013", 9 pgs.
"International Application Serial No. PCT/US2011/045044, International Search Report dated Nov. 3, 2011", 4 pgs.
"International Application Serial No. PCT/US2011/045044, Written Opinion dated Nov. 3, 2011", 9 pgs.
"International Application Serial No. PCT/US2012/058741, International Preliminary Report on Patentability dated Apr. 17, 2014", 6 pgs.
"International Application Serial No. PCT/US2012/058741, International Search Report dated Feb. 6, 2013", 5 pgs.
"International Application Serial No. PCT/US2012/058741, Written Opinion dated Feb. 6, 2013", 4 pgs.
"International Application Serial No. PCT/US2012/069902, International Preliminary Report on Patentability dated Jun. 26, 2014", 10 pgs.
"International Application Serial No. PCT/US2012/069902, International Search Report dated Aug. 22, 2013", 6 pgs.
"International Application Serial No. PCT/US2012/069902, Written Opinion dated Aug. 22, 2013", 9 pgs.
"NK 2012 Abstracts", (2012), 12 pgs.
Bartel, David P., et al., "Isolation of New Ribozymes from a Large Pool of Random Sequence", *Science*, 261(5127), (1993), 1411-1418.
Baucher, Marie, et al., "Lignin: Genetic Engineering and Impact on Pulping", *Crit. Rev. Biochem. Mol. Biol.*, 38(4), (2003), 305-350.
Bedell, J. A, et al., "Sorghum Genome Sequencing by Methylation Filtration", *PLoS Biol.*, 3(1): e13, (2005), 0103-0115.
Beuerle, Till, et al., "Enzymatic Synthesis and Purification of Aromatic Coenzyme A Esters", *Anal. Biochem.*, 302(2), (2002), 305-312.
Beurerle, Till, et al., "Enzymatic Synthesis and Purification of Aromatic Coenzyme A Esters", *Analytical Biochemistry*, vol. 302, doi:10.1006/abio.2001.5574, (22002), 305-312.
Blumenkrantz, Nelly, et al., "New Method for Quantitative Determination of Uronic Acids", *Anal. Biochem.*, 54(2), (1973), 484-489.
Boerjan, Wout, et al., "Lignin Biosynthesis", *Annu. Rev. Plant Biol.*, 54, (2003), 519-546.
Del Rio, Jose C., et al., "Highly Acylated (Acetylated and/or p-Coumaroylated) Native Lignins from Diverse Herbaceous Plants", *J. Agr. Food Chem.*, 56(20), (2098), 9525-9534.
Dien, Bruce S., et al., "Chapter 23. Converting Herbaceous Energy Crops to Bioethanol: A Review with Emphasis on Pretreatment Processes", In: *Handbook of Industrial Biocatalysis*, Hou, Ching T., CRC Press, LLC, Boca Raton, FL, (2005), 23-1-23-11.

Dien, Bruce S., et al., "Chemical composition and response to dilute-acid pretreatment and enzymatic saccharification of alfalfa, reed canarygrass, and switchgrass", *Biomass and Bioenergy*, 30(10), (2006), 880-891.
Donaldson, Lloyd A., et al., "Lignification and lignin topochemistry—an ultrastructural view", *Phytochemistry*, 57, (2001), 859-873.
Fukushima, Romualdo S., et al., "Comparison of the Acetyl Bromide Spectrophotometric Method with Other Analytical Lignin Methods for Determining Lignin Concentration in Forage Samples", *J. Agric. Food Chem.*, 52, (2004), 3713-3720.
Grabber, J. H., et al., "p-Coumaroylated syringyl units in maize lignin; implications for β-ether cleavage by thioacidolysis", *Phytochem.* 43(6), (1996), 1189-1194.
Grabber, John H., et al., "Apoplastic pH and Monolignol Addition Rate Effects on Lignin Formation and Cell Wall Degradability in Maize", *J. Agric. Food Chem.*, 51, (2003), 4984-4989.
Grabber, John H., et al., "Coniferyl Ferulate Incorporation into Lignin Enhances the Alkaline Delignification and Enzymatic Degradation of Cell Walls", *Biomacromolecules*, 9, (2008), 2510-2516.
Grabber, John H, et al., "Coniferyl Ferulate Incorporation into Lignin Enhances the Alkaline Delignification and Enzymatic Degradation of Cell Walls", Biomacromolecules Sep. 2008 *American Chemical Society* US, vol. 9, No. 9, (2008), 2510-2516.
Grabber, John H., et al., "Cross-Linking of Maize Walls by Ferulate Dimerization and Incorporation into Lignin", *J. Agric. Food Chem.*, 48, (2000), 6106-6113.
Grabber, John H., et al., "Dehydrogenation Polymer-Cell Wall Complexes as a Model for Lignified Grass Walls", *J. Agric. Food Chem.*, 44, (1996), 1453-1459.
Grabber, John H., et al., "Ferulate cross-linking in cell walls isolated from maize cell suspensions", *Phytochemistry*, 40(4), (1995), 1077-1082.
Grabber, John H., et al., "Ferulate Cross-Links Limit the Enzymatic Degradation of Synthetically Lignified Primary Walls of Maize", *J. Agric. Food Chem.*, 46, (1998), 2609-2614.
Grabber, John H., et al., "Formation of syringyl-rich lignins in maize as influenced by feruloylated xylans and p-coumaroylated monolignols", *Planta*, 226(3), (2007), 741-751.
Grabber, John H., "How Do Lignin Composition, Structure, and Cross-Linking Affect Degradability? A Review of Cell Wall Model Studies", *Crop. Sci.*, 45, (2005), 820-831.
Grabber, John H., et al., "Model Studies of Ferulate-Coniferyl Alcohol Cross-Product Formation in Primary Maize Walls: Implications for Lignification in Grasses", *J. Agric. Food Chem.*, 50, (2002), 6008-6016.
Gratzl, Josef S., et al., "Chapter 20—Chemistry of Pulping: Lignin Reactions", In: Lignin: Historical, Biological, and Materials Perspectives, *ACS Symposium Series*, vol. 742, (2000), 392-421.
Hartley, R. D, "p-Coumaric and ferulic acid components of cell walls of ryegrass and their relationships with lignin and digestibility", *J. Sci. Food. Agric.*, 23(11), (1972), 1347-1354.
Hartley, Roy D., "Monomeric and Dimeric Phenolic Acids Released from Cell Walls of Grasses by Sequential Treatment with Sodium Hydroxide", *J. Sci. Food Agric.*, 55(3), (1991), 365-375.
Hatfield, R. D., et al., "Composition of cell walls isolated from cell types of grain sorghum stems", *J. Sci. Food Agric.*, 79, (1999), 891-899.
Hatfield, R. D., et al., "Degradation Characteristics of Isolated and In Situ Cell Wall Lucerne Pectic Polysaccharides by Mixed Ruminal Microbes", *J. Sci. Food Agric.*, 69, (1995), 185-196.
Hatfield, R. D. et al., "Enzymatic processes involved in the incorporation of hydroxycinnamates into grass cell walls", *Phyochemistry Reviews*, 9(1), (2010), 35-45.
Hatfield, R. D., et al., "Grass lignin acylation: p-cournaroyl transferase activity and cell wall characteristics of C3 and C4 grasses", *Planta*, 229(6), (2009), 1253-1267.
Hatfield, R. D., et al., "Using the Acetyl Bromide Assay to Determine Lignin Concentrations in Herbaceous Plants: Some Cautionary Notes", *J. Agric. Food Chem.*, 47(2), (1999), 628-632.
Hatfield, Ronald D., et al., "A Comparison of the Insoluble Residues Produced by the Klason Lignin and Acid Detergent Lignin Procedures", *J Sci Food Agric.*, 65, (1994), 51-58.

(56) References Cited

OTHER PUBLICATIONS

Hatfield, Ronald, et al., "A potential role for sinapyl p-coumarate as a radical transfer mechanism in grass lignin formation", *Planta*, 228, (2008), 919-928.

Helm, Richard F., et al., "Synthesis of feruloylated and p-coumaroylated methyl glycosides", *Carbohydrate Research*, 229(1), (1992), 183-194.

Howard, R. L., et al., "Lignocellulose biotechnology: issues of bioconversion and enzyme production", *African Journal of Biotechnology*, 2(12), (2003), 602-619.

Hsiao, Jeh-Jian, et al., "Lignans from the Wood of *Aralia bipinnata*", *Phytochemistry*, 39(4), (1995), 899-902.

Irmak, Sibel, et al., "Hydrogen rich gas production by thermocatalytic decomposition of kenaf biomass", *International Journal of Hydrogen Energy*, vol. 35, No. 11, (2010), 5312-5317.

Kim, Hoon, et al., "Solution-state 2D NMR of Ball-milled Plant Cell Wall Gels in DMSO-$d_6$", *BioEnergy Research*, 1, (2008), 56-66.

Kubes, G. J., et al., "Alkaline pulping with additives. A review", *Wood Sci. Technol.*, 14, (1980), 207-228.

Li, Song-Lin, et al., "Time-Course Accumulation of Main Bioactive Components in the Rhizome of *Ligusticum chuanxiong*", *Planta Med.*, 72, (2006), 278-280.

Lu, Fachuang, et al., "Detection and Determination of p-Coumaroylated Units in Lignins", *J. Agric. Food Chem.*, 47, (1999), 1988-1992.

Lu, Fachuang, et al., "Facile Synthesis of 4-Hydroxycinnamyl p-Coumarates", *J. Agric. Food Chem.*, 46(8), (1998), 2911-2913.

Lu, Fachuang, et al., "Highly Selective Syntheses of Coniferyl and Sinapyl Alcohols", *J. Agric. Food Chem.*, 46, (1998), 1794-1796.

Lu, Fachuang, et al., "Novel β-β-structures in lignins incorporating acylated monolignols", In: Proceedings, *Thirteenth International Symposium on Wood, Fiber, and Pulping Chemistry*, vol. 3, APPITA, Auckland, New Zealand, (2005), 233-237.

Lu, Fachuang, et al., "Novel tetrahydrofuran structures derived from β-β-coupling reactions involving sinapyl acetate in Kenaf lignins", *Org. Biomol. Chem.*, 6(20), (2008), 3681-3694.

Lu, Fachuang, et al., "Preliminary evidence for sinapyl acetate as a lignin monomer in kenaf", *Chemical Communications*, Issue 1, (2002), 90-91.

Majcerczyk, Andrzej, et al., "Size-exclusion chromatography of lignin as ion-pair complex", *Journal of Chromatography A*, 764(2), (1997), 183-191.

Meyermans, Hugo, et al., "Modifications in Lignin and Accumulation of Phenolic Glucosides in Poplar Xylem upon Down-regulation of Caffeoyl-Coenzyme A O-Methyltransferase, an Enzyme involved in Lignin Biosynthesis", *The Journal of Biological Chemistry*, 275(47), (2000), 36899-36909.

Mitchell, Rowan A, et al., "A Novel Bioinformatics Approach Identifies Candidate Genes for the Synthesis and Feruloylation of Arabinoxylan", *Plant Physiology*, 144(1), (2007), 43-53.

Murnen, H. K., et al., "Optimization of Ammonia Fiber Expansion (AFEX) Pretreatment and Enzymatic Hydrolysis of Miscanthus x Giganteus to Fermentable Sugars", *Biotechnol. Prog.*, 23(4), (2007), 846-850.

Nakamura, Y., et al., "Ester linkage of p-coumaric acid in bamboo lignin. III. Dehydrogenative polymerization of coniferyl p-hydroxybenzoate and coniferyl p-coumarate", *Cellulose Chem. Technol.*, 12(2), (1978), 209-221.

Nakano, J., et al., "Studies on lignin. XXXII. Ester groups of lignin", *Tappi*, 44(1), (1961), 30-32.

Oosterveld, Alexander, et al., "Formation of ferulic acid dehydrodimers through oxidative cross-linking of sugar beet pectin", *Carbohydrate Research*, 300, (1997), 179-181.

Paula, Vanderlucia F., et al., "Lignans from *Ochroma lagopus* Swartz", *Tetrahedron*, 51(45), (1995), 12453-12462.

Ralph, J., et al., "Effects of Coumarate 3-Hydroxylase Down-regulation on Lignin Structure", *The Journal of Biological Chemistry*, 281(13), (2006), 8843-8853.

Ralph, John, "An Unusual Lignin from Kenaf", *Journal of Natural Products*, 59(4), (1996), 341-342.

Ralph, John, "Hydroxycinnamates in lignification", *Phytochemistry Reviews*, vol. 9, No. 1, (Jan. 1, 2010), 65-83.

Ralph, John, et al., "Lignin-ferulate cross-links in grasses: active incorporation of ferulate polysaccharide esters into ryegrass lignins", *Carbohydrate Research*, 275(1), (1995), 167-178.

Ralph, John, et al., "Lignin-Feruloyl Ester Cross-Links in Grasses. Part 1. Incorporation of Feruloyl Esters into Coniferyl Alcohol Dehydrogenation polymers", *Journal of the Chemical Society, Perkin Transactions 1*, Issue 21, (1992), 2961-2969.

Ralph, John, et al., "Lignins: Natural polymers from oxidative coupling of 4-hydroxyphenyl-propanoids", *Phytochemistry Reviews*, 3(1), (2004), 29-60.

Ralph, John, et al., "Methods of Modifying Lignin Structure", U.S. Appl. No. 61/213,706, filed Jul. 6, 2009, 92 pgs.

Ralph, John, et al., "Pathway of p-Coumaric Acid Incorporation into Maize Lignin as Revealed by NMR", *J. Am. Chem. Soc.*, 116, (1994,), 9448-9456.

Ralph, John, et al., "Peroxidase-dependent cross-linking reactions of p-hydroxycinnamates in plant cell walls", *Phytochemistry Reviews*, 3, (2004), 79-96.

Ralph, John, et al., "The DFRC Method for Lignin Analysis. 6. A Simple Modification for Identifying Natural Acetates on Lignins", *J. Agric. Food Chem.*, 46, (1998), 4616-4619.

Ralph, John, "What Makes a Good Monolignol Substitute?", In: *The Science and Lore of the Plant Cell Wall*, Hayashi, T., Editor, Brown Walker Press, Boca Raton, FL, (2006), 285-293.

Ralph, Sally A., et al., "NMR Database of Lignin and Cell Wall Model Compounds", [online]. [archived on Feb. 24, 2013]. Retrieved from the Internet: <URL: https://web.archive.org/web/20130224043206/http://ars.usda.gov/Services/docs.htm?docid=10491>, (Nov. 2004), 2 pgs.

Santoro, Nicholas, et al., "A high-throughput screening assay for the carboxyltransferase subunit of acetyl-CoA carboxylase", *Anal. Biochem.*, 354(1), (2006), 70-77.

Sato, Yutaka, et al., "Field transcriptome revealed critical developmental and physiological transitions involved in the expression of growth potential in *Japonica* rice", *BMC Plant Biology* 11(10), (2011), 1-15.

Sato, Yutaka, "RiceXPro: a platform for monitoring gene expression in *Japonica* rice grown under natural field conditions", *Nucleic Acids Research*, 39(Sippl. 1), (2011), D1141-D1148.

Seca, Ana M. L., et al., "Phenolic constituents from the core of Kenaf (*Hibiscus cannabinus*)", *Phytochemistry*, 56, (2001), 759-767.

Selvendran, R. R., et al., "2. Developments in the Isolation and Analysis of Cell Walls From Edible Plants", In: *Biochemistry of Plant Cell Walls*, Brett, C. T., et al., Editors, Cambridge University Press, Cambridge, MA, (1985), 39-78.

Shatalov, A. A., et al., "*Arundo donax* L. reed: new perspectives for pulping and bleaching. Part 4. Peroxide bleaching of organosolv pulps.", *Bioresource Technology*, 96(8), (2005), 865-872.

Shea, Elaine M., et al., "Characterization of a Pectic Fraction from Smooth Bromegrass Cell Walls Using an Endopolygalacturonase", *J. Agric. Food Chem.*, 41, (1993), 380-307.

Shimada, Mikio, et al., "Ester Linkages of p-Coumaric Acide in Bamboo and Grass Lignins", *Tappi*, 54(1), (Jan. 1971), 72-78.

Simmons, Blake A, et al., "Advances in modifying lignin for enhanced biofuel production", *Current Opinion in Plant Biology, Quadrant Subscription Services*, vol. 13, No. 3, (2010), 313-320.

Smith, D. C. C., "p-Hydroxybenzoates groups in the lignin of Aspen (*Populus tremula*)", *J. Chem. Soc.*,, (1955), 2347-2351.

Sun, R. C., et al., "Fractional Isolation and Structural Characterization of Lignins from Oil Palm Trunk and Empty Fruit Bunch Fibers", *Journal of Wood Chemistry and Technology*, 19(4), (1999), 335-356.

Vanholme, Ruben, et al., "Lignin engineering", *Current Opinion in Plant Biology*, 11, (2008), 278-285.

Vogel, John P, et al., "EST sequencing and phylogenetic analysis of the model grass *Brachypodium distachyon*", *Theoretical and Applied Genetics*, 113(2), (2006), 186-195.

(56) References Cited

OTHER PUBLICATIONS

Wagner, Armin, et al., "CCoAOMT suppression modifies lignin composition in *Pinus radiata*", *The Plant Journal*, 67(1), (2011), 119-129.
Webber, et al., "United States kenaf (*Hibiscus cannabinus* L.) cultivar review", *Plant Fibers as Renewable Feedstocks for Biofuel and Bio-Based Products*, (Sep. 6, 2011), 117-126.
Wilkerson, C. G., et al., "Monolignol Frerulate Transferase Introduces Chemically Labile Linkages into the Lignin Backbone", *Science*, 344(6179), 90-93, and Supplementary Materials, (2014), 34 pgs.
Withers, S., et al., "Identification of Grass-specific Enzyme That Acylates Monolignols with p-Coumarate", *Journal of Biological Chemistry*, 287(11), (2012), 8347-8355.
Xie, Jing-Jing, et al., "Optimization and Comparison of Five Methods for Extraction of Coniferyl Ferulate from Angelica sinensis", *Molecules*, vol. 14, No. 1, (2009), 555-565.
Xie, Jing-Jing, et al., "Optimization and Comparison of Five Methods for Extraction of Coniferyl Ferulate from Angelica sinensis", *Molecules*, 14(1), (2009), 555-565.
Zhong, Ruiqin, et al., "A Battery of Transcription Factors Invloved in the REgulation of Secondary Cell Wall Biosynthese in *Arabidopsis*", *The Plant Cell*, vol. 20, (2008), 2763-2782.
"U.S. Appl. No. 14/365,744, Response filed Feb. 16, 2018 to Final Office Action dated Nov. 27, 2017", 18 pgs.
"U.S. Appl. No. 15/285,182, Response filed Mar. 6, 2018 to Non Final Office Action dated Dec. 12, 2017", 7 pgs.
"GRMZM2G028104(umc1739)—Classical Gene List", MaizeGDB Gene Record Page, [Online]. [Accessed Feb. 15, 2018]. Retrieved from the Internet: <URL: https://www.maizegdb.org/gene_center/gene/GRMZM2G028104>, 8 pgs.
Garcia-Cerdian, Jose G., et al., "The PsbW proteiin stabilizes the supramolecular organization of photosystem II in higher plants", The Plant Journal (2011) 65, 368-381, (2011), 368-381.
Nahid, Nazia, et al., "RNA interference-based resistance against a legume mastrevirus", Virology Journal, 8: 499, (2011), 8 pgs.
Radziejwoski, Amandine, et al., "Atypical E2F activity coordinates PHR1 photolyase gene transcription with endoreduplication onset", The EMBO Journal, 30, (2011), 355-363.
"U.S. Appl. No. 14/365,744, Final Office Action dated Nov. 27, 2017", 17 pgs.
"U.S. Appl. No. 14/365,744, Non Final Office Action dated May 25, 2017", 16 pgs.
"U.S. Appl. No. 14/365,744, Response filed Aug. 25, 2017 to Non Final Office Action dated May 25, 2017", 16 pgs.
"U.S. Appl. No. 14/365,744, Response filed Restriction Requirement dated Dec. 2, 2016", 11 pgs.
"U.S. Appl. No. 14/365,744, Restriction Requirement dated Dec. 2, 2016", 12 pgs.
"U.S. Appl. No. 15/285,182, Non Final Office Action dated Dec. 12, 2017", 11 pgs.
"Austrailian Application Serial No. 2012318626, First Examiners Report dated May 25, 2017", 2 pgs.
"Austrailian Application Serial No. 2012318626, Response Filed Jun. 28, 2017 to First Examiners Report dated May 25, 2017", 13 pgs.
"Canadian Application Serial No. 2,806,481, Office Action dated Jan. 18, 2018", 3 pgs.
"Canadian Application Serial No. 2,806,481, Office Action dated Nov. 21, 2016", 5 pgs.
"Canadian Application Serial No. 2,806,481, Response Filed May 18, 2017 to Office Action dated Nov. 21, 2016", 18 pgs.
"Canadian Application Serial No. 2,851,231, Office Action dated Nov. 28, 2016", 5 pgs.
"Canadian Application Serial No. 2,851,231, Response Filed May 29, 2017 to Office Action dated Nov. 28, 2016", 9 pgs.
"Canadian Application Serial No. 2,851,231, Voluntary Amendment filed Jan. 8, 2018", 4 pgs.
"Canadian Application Serial No. 2,859,564, Office Action dated Nov. 28, 2016", 4 pgs.
"Canadian Application Serial No. 2,859,564, Office Action dated Dec. 14, 2017", 4 pgs.
"Canadian Application Serial No. 2,859,564, Response Filed May 29, 2017 to Office Action dated Nov. 28, 2016", 15 pgs.
"Chile Application Serial No. 843-14, Office Action dated Mar. 13, 2017", (W/ English Translation), 21 pgs.
"Chile Application Serial No. 843-14, Response Filed May 26, 2017 to Office Action dated Mar. 13, 2017", (W/O English Claims), 7 pgs.
"Chile Application Serial No. 843-2014, Office Action dated Jul. 27, 2017", 10 pgs.
"Chile Application Serial No. 843-2014, Response Filed Oct. 30, 2017 to Office Action dated Jul. 27, 2017", (W/O English Claims), 6 pgs.
"European Application Serial No. 12772693.3, Communication Pursuant to Article 94(3) EPC dated Feb. 13, 2017", 4 pgs.
"European Application Serial No. 12772693.3, Communication Pursuant to Article 94(3) EPC dated Aug. 18, 2016", 4 pgs.
"European Application Serial No. 12772693.3, Response Filed May 31, 2017 to Communication Pursuant to Article 94(3) EPC dated Feb. 13, 2017", 21 pgs.
"European Application Serial No. 12772693.3, Response filed Oct. 27, 2016 to Communication Pursuant to Article 94(3) EPC dated Aug. 18, 2016", 8 pgs.
"European Application Serial No. 16193228.0, Communication Pursuant to Article 94(3) EPC dated Nov. 28, 2017", 4 pgs.
"European Application Serial No. 16193228.0, Extended European Search Report dated Dec. 9, 2016", 9 pgs.
"European Application Serial No. 16193228.0, Response filed Sep. 1, 2017 to Extended European Search Report dated Dec. 9, 2016", 9 pgs.
"European Patent Application No. 12772693.3, Indication of deficiencies in a request pursuant to Rule 22 EPC and invitation to correct them dated Jul. 7, 2017", 2 pgs.
"European Patent Application No. 12772693.3, Response Filed Sep. 20, 2017 to Indication of deficiencies in a request pursuant to Rule 22 EPC and invitation to correct them dated Jul. 7, 2017", 2 pgs.
Friedberg, "Automated protein function prediction—the genomic challenge.", Brief. Bioinformatics, 7(3), (2006), 225-242.
"European Application Serial No. 16193228.0, Response filed Mar. 23, 2018 to Communication Pursuant to Article 94(3) EPC dated Nov. 28, 2017", 98 pgs.

\* cited by examiner

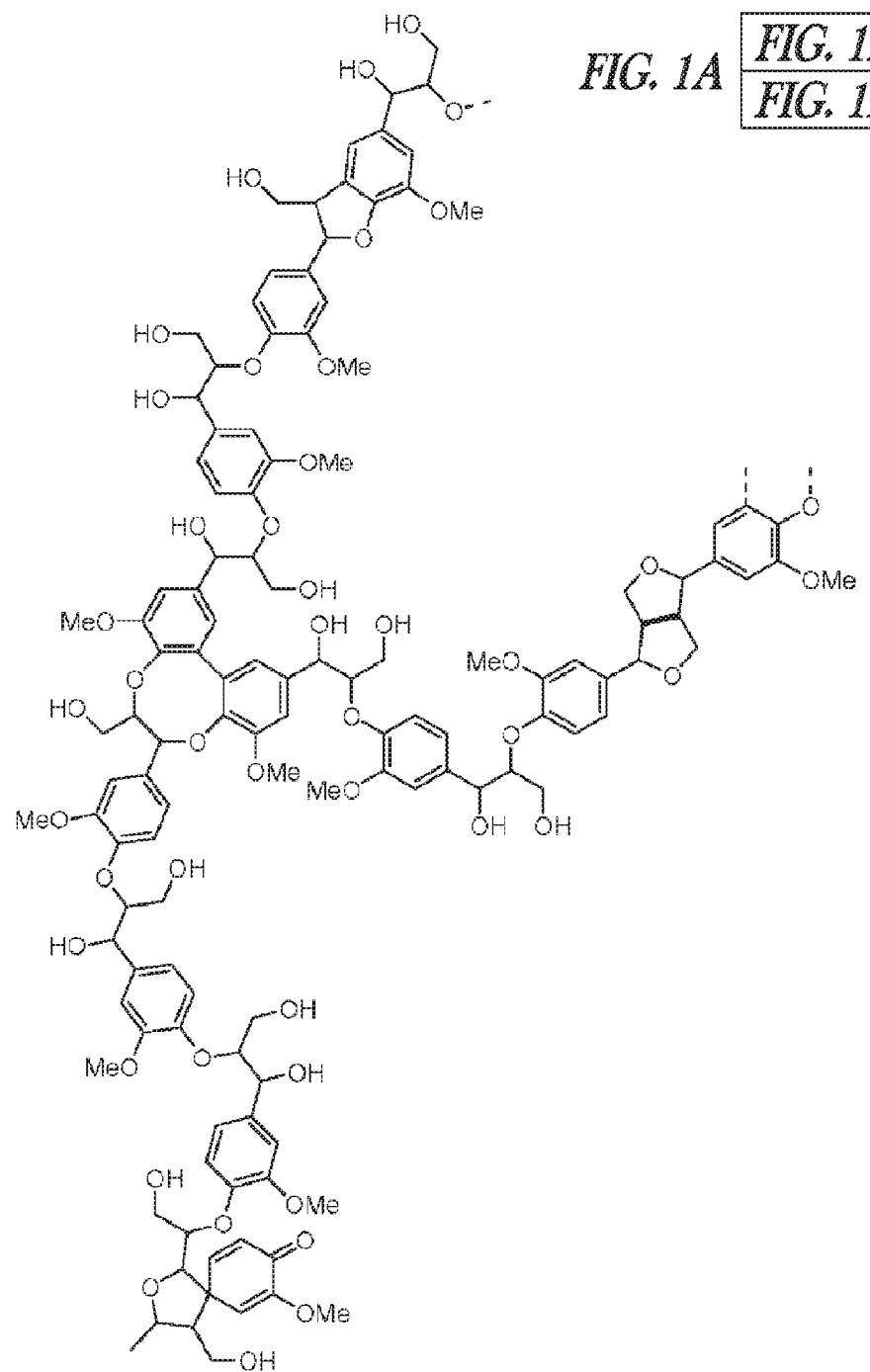
FIG. 1A1

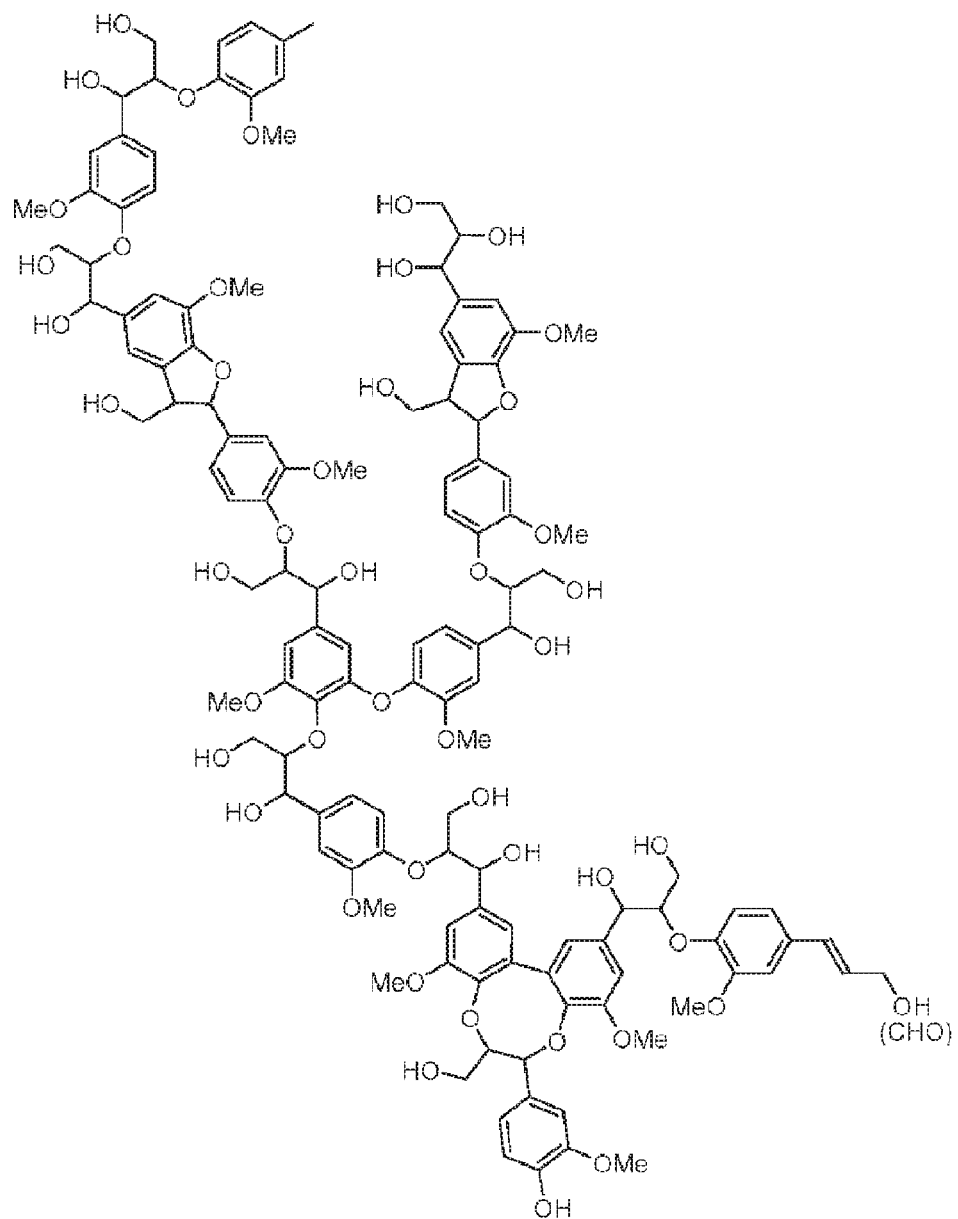
FIG. 1A2

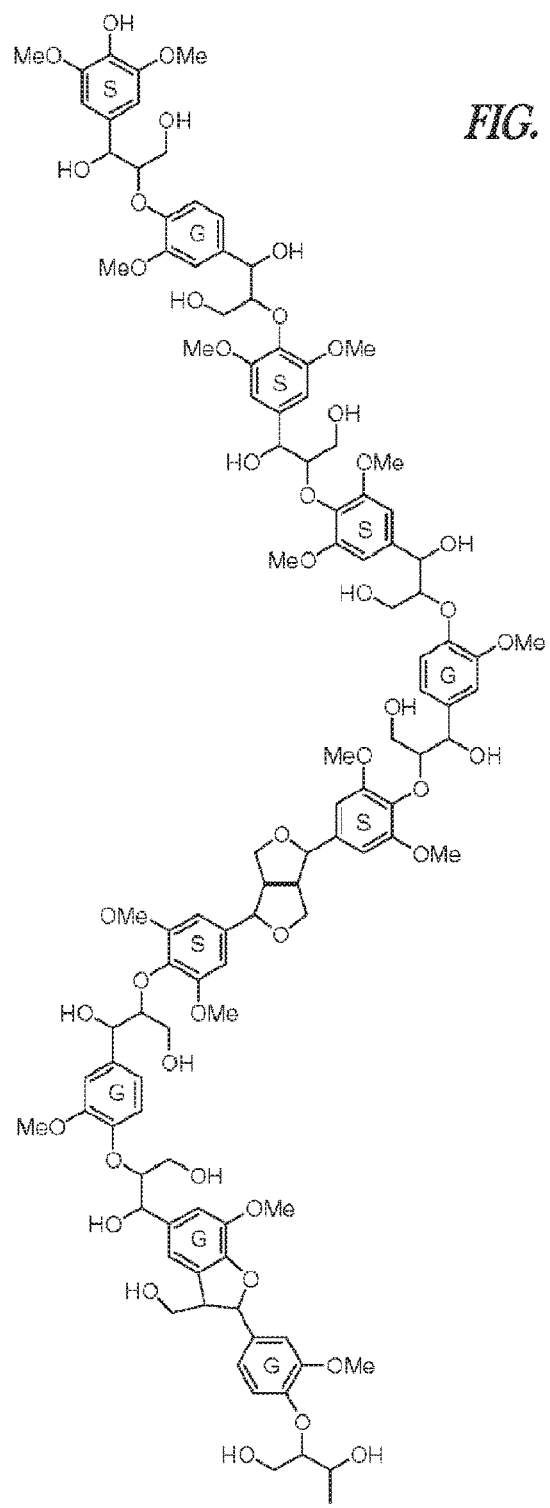
FIG. 1B1

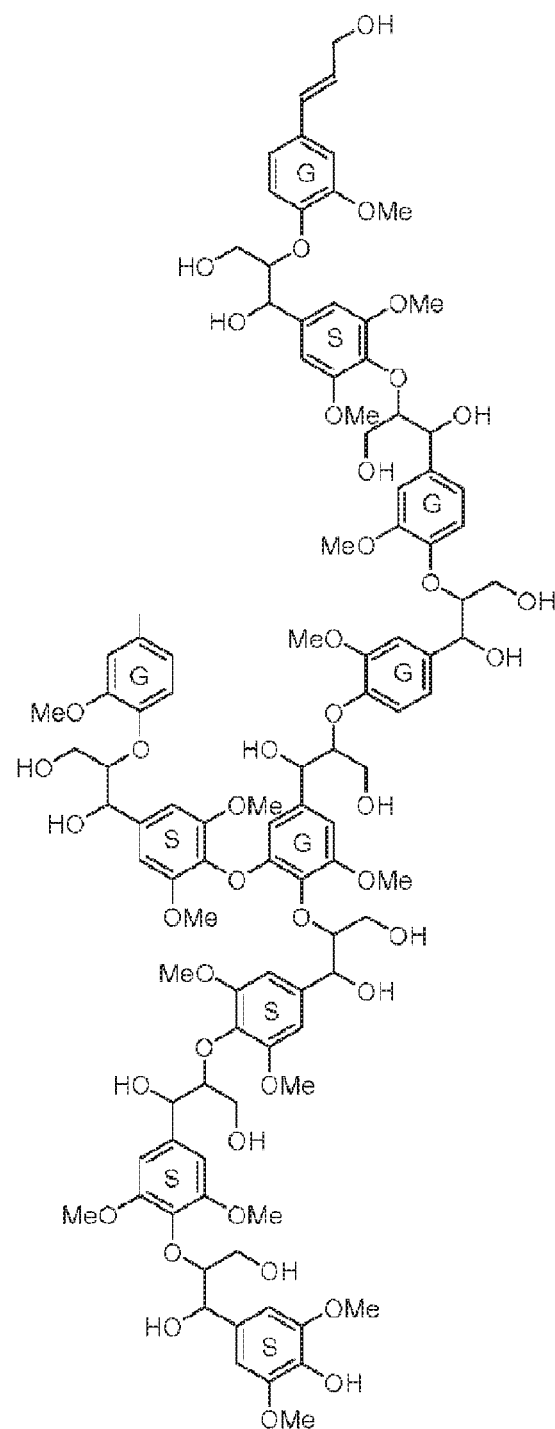
FIG. 1B2

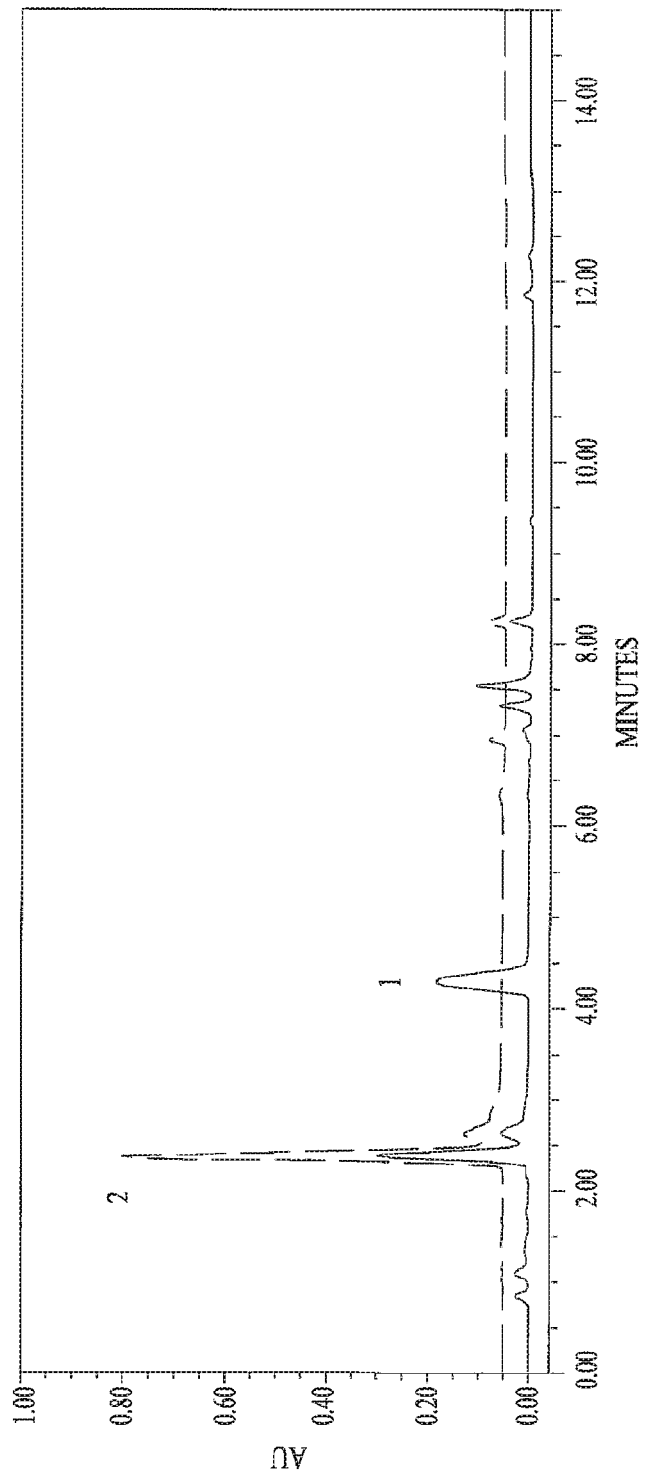

```
                              SEQUENCE LISTING

<160> NUMBER OF SEQ ID NOS: 7

<210> SEQ ID NO 1
<211> LENGTH: 1326
<212> TYPE: DNA
<213> ORGANISM: Angelica sinensis

<400> SEQUENCE: 1
atgacgatca tggaggttca agttgtatct aagaagatgg taaagccatc agttccgact      60
cctgaccacc acaagacttg caaattgacg gcattcgatc agattgctcc tccggatcaa     120
gttcccatta tttacttcta acagcagc aacatccaca atattcgcga gcaattggta       180
aaatccttgt ccgaaactct aaccaagttt tatccattag ctggaagatt tgttcaagat     240
ggtttctatg tcgattgtaa tgatgaaggg gtcttgtacg tagaagctga agttaacatt     300
ccgctaaacg aattcatcgg acaagcaaag aaaaatatac aacttatcaa tgatcttgtt    360
ccgaaaaaaa acttcaagga tattcattca tatgaaaatc caatagtggg attacagatg    420
agttatttca agtgtggtgg acttgctatt tgcatgtatc tttcgcatgt tgtagctgat    480
ggatatacag cagcagcatt cactaaagag tggtctaaca caaccaatgg catcatcaat    540
ggcgatcaac tagtttcttc ttctccgatt aacttcgaat ggcaactct agtcccagct    600 agagatttat cgacggtgat caagccagcc gtgatgccac catcaaagat caaggaaacc    660
aaggttgtca aaggaggtt tctgttcgat gaaaatgcga tatcagcttt caaagaccat    720
gtcatcaaat ccgaaagcgt taaccggcct acacgggtgg aagttgtgac atctgtgtta    780
tggaaggctc tgatcaacca gtctaagctt ccaagttcta cactatattt tcacctcaac    840
tttagaggga aaacaggcat caacacccca ccgctagata tcatttttc gctttgcgga    900 aacttttaca ctcaggttcc tacaaggttc agggggggaa atcaaacaaa acaggatttg    960
gaattgcatg aattggtcaa gttgttgaga ggaaagttgc gtaacactct gaagaattgc   1020
tccgaaatta acactgccga tgggctgttc ctggaagcag ctagtaattt caatattata   1080
caggaagatt tggaggacga acaagtggat gttcggattt ttacaacgtt gtgtaggatg    1140
cctttgtatg aaactgagtt tgggtgggga aaaccagaat gggttaccat tccagagatg    1200
catttggaga tagtgtttct tttggacact aaatgtggga ctggtattga ggcattagtg    1260
agcatggatg aagcagatat gcttcagttt gaacttgatc ccaccatctc tgctttcgct    1320
tcctag                                                              1326

<210> SEQ ID NO 2
<211> LENGTH: 441
<212> TYPE: PRT
<213> ORGANISM: Angelica sinensis

<400> SEQUENCE: 2

Met Thr Ile Met Glu Val Gln Val Val Ser Lys Lys Met Val Lys Pro
  1               5                  10                  15

Ser Val Pro Thr Pro Asp His His Lys Thr Cys Lys Leu Thr Ala Phe
             20                  25                  30

Asp Gln Ile Ala Pro Pro Asp Gln Val Pro Ile Ile Tyr Phe Tyr Asn
         35                  40                  45

Ser Ser Asn Ile His Asn Ile Arg Glu Gln Leu Val Lys Ser Leu Ser
     50                  55                  60

Glu Thr Leu Thr Lys Phe Tyr Pro Leu Ala Gly Arg Phe Val Gln Asp
```

```
                65                  70                  75                  80
            Gly Phe Tyr Val Asp Cys Asn Asp Glu Gly Val Leu Tyr Val Glu Ala
                            85                  90                  95

Glu Val Asn Ile Pro Leu Asn Glu Phe Ile Gly Gln Ala Lys Lys Asn
                            100                 105                 110

Ile Gln Leu Ile Asn Asp Leu Val Pro Lys Lys Asn Phe Lys Asp Ile
                            115                 120                 125

His Ser Tyr Glu Asn Pro Ile Val Gly Leu Gln Met Ser Tyr Phe Lys
                            130                 135                 140

Cys Gly Gly Leu Ala Ile Cys Met Tyr Leu Ser His Val Val Ala Asp
            145                 150                 155                 160

Gly Tyr Thr Ala Ala Ala Phe Thr Lys Glu Trp Ser Asn Thr Thr Asn
                            165                 170                 175

Gly Ile Ile Asn Gly Asp Gln Leu Val Ser Ser Pro Ile Asn Phe
                            180                 185                 190

Glu Leu Ala Thr Leu Val Pro Ala Arg Asp Leu Ser Thr Val Ile Lys
                            195                 200                 205

Pro Ala Val Met Pro Pro Ser Lys Ile Lys Glu Thr Lys Val Val Thr
                            210                 215                 220

Arg Arg Phe Leu Phe Asp Glu Asn Ala Ile Ser Ala Phe Lys Asp His
            225                 230                 235                 240

Val Ile Lys Ser Glu Ser Val Asn Arg Pro Thr Arg Val Glu Val Val
                            245                 250                 255

Thr Ser Val Leu Trp Lys Ala Leu Ile Asn Gln Ser Lys Leu Pro Ser
                            260                 265                 270

Ser Thr Leu Tyr Phe His Leu Asn Phe Arg Gly Lys Thr Gly Ile Asn
                            275                 280                 285

Thr Pro Pro Leu Asp Asn His Phe Ser Leu Cys Gly Asn Phe Tyr Thr
                            290                 295                 300

Gln Val Pro Thr Arg Phe Arg Gly Gly Asn Gln Thr Lys Gln Asp Leu
            305                 310                 315                 320

Glu Leu His Glu Leu Val Lys Leu Leu Arg Gly Lys Leu Arg Asn Thr
                            325                 330                 335

Leu Lys Asn Cys Ser Glu Ile Asn Thr Ala Asp Gly Leu Phe Leu Glu
                            340                 345                 350

Ala Ala Ser Asn Phe Asn Ile Ile Gln Glu Asp Leu Glu Asp Glu Gln
                            355                 360                 365

Val Asp Val Arg Ile Phe Thr Thr Leu Cys Arg Met Pro Leu Tyr Glu
                            370                 375                 380

Thr Glu Phe Gly Trp Gly Lys Pro Glu Trp Val Thr Ile Pro Glu Met
            385                 390                 395                 400

His Leu Glu Ile Val Phe Leu Leu Asp Thr Lys Cys Gly Thr Gly Ile
                            405                 410                 415

Glu Ala Leu Val Ser Met Asp Glu Ala Asp Met Leu Gln Phe Glu Leu
                            420                 425                 430

Asp Pro Thr Ile Ser Ala Phe Ala Ser
                            435                 440

<210> SEQ ID NO 3
<211> LENGTH: 48
<212> TYPE: DNA
<213> ORGANISM: Artificial Sequence
<220> FEATURE:
<223> OTHER INFORMATION: A synthetic primer
```

```
<400> SEQUENCE: 3
tagaggccga ggcggccgac atgttttgtt ttttttctt ttttttt                48

<210> SEQ ID NO 4
<211> LENGTH: 39
<212> TYPE: DNA
<213> ORGANISM: Artificial Sequence
<220> FEATURE:
<223> OTHER INFORMATION: A synthetic primer

<400> SEQUENCE: 4
aaaaaagcag gcttcatgac gatcatggag gttcaagtt                        39

<210> SEQ ID NO 5
<211> LENGTH: 39
<212> TYPE: DNA
<213> ORGANISM: Artificial Sequence
<220> FEATURE:
<223> OTHER INFORMATION: A synthetic primer

<400> SEQUENCE: 5
gtacaagaaa gctgggttct aggaagcgaa agcagagat                        39

<210> SEQ ID NO 6
<211> LENGTH: 29
<212> TYPE: DNA
<213> ORGANISM: Artificial Sequence
<220> FEATURE:
<223> OTHER INFORMATION: A synthetic primer

<400> SEQUENCE: 6
ggggacaagt ttgtacaaaa aagcaggct                                   29

<210> SEQ ID NO 7
<211> LENGTH: 28
<212> TYPE: DNA
<213> ORGANISM: Artifical Sequence
<220> FEATURE:
<223> OTHER INFORMATION: A synthetic primer

<400> SEQUENCE: 7
gggaccactt tgtacaagaa agctgggt                                    28
```

FERULOYL-CoA:MONOLIGNOL TRANSFERASE

This application is a continuation of U.S. patent application Ser. No. 13/811,823, filed May 8, 2013, which is a U.S. National Stage Application filed under 35 U.S.C. § 371 of International Patent Application No. PCT/US2011/044981, filed on Jul. 22, 2011, and published on May 4, 2012 as WO 2012/012698A1, which applications claim benefit of the priority filing date of U.S. Patent Application Ser. No. 61/366,977, filed Jul. 23, 2010, the contents of all of which are specifically incorporated herein by reference in their entirety. This application is also related to published U.S. patent application Ser. No. 12/830,905, filed Jul. 6, 2010 and to U.S. Patent Application Ser. No. 61/213,706, filed Jul. 6, 2009, the contents of both of which are specifically incorporated herein by reference in their entireties.

This invention was made with government support under DE-FC02-07ER64494 awarded by the U.S. Department of Energy. The government has certain rights in the invention.

This invention was made as a result of activities undertaken within the scope of a Joint Research Agreement between Michigan State University and Wisconsin Alumni Research Foundation.

BACKGROUND OF THE INVENTION

Lignin is an important cell wall component that provides structural support to plants and is needed for plant vascular tissue function. It is one of the most abundant organic polymers on Earth, constituting about 30% of non-fossil organic carbon and from a quarter to a third of the dry mass of wood. Because the chemical structure of lignin is difficult to degrade by chemical and enzymatic means, lignin makes the task of producing paper and biofuels from plant cell walls difficult.

SUMMARY OF THE INVENTION

The invention relates to the identification and isolation of new acyltransferase nucleic acids and polypeptides. The acyltransferase enzyme is a feruloyl-CoA:monolignol transferase (FMT, also called a monolignol ferulate transferase) that produces monolignol ferulates, which can be used for making plants that contain a readily cleavable lignin. Use of the feruloyl-CoA:monolignol transferase nucleic acids and/or polypeptides in plants can simplify the processes used for making biofuels and paper from those plants because these plants have lignin that is more readily removed by chemical (pre)treatment. No other cloned or isolated enzyme with these beneficial properties is currently available.

One aspect of the invention is an isolated nucleic acid encoding a feruloyl-CoA:monolignol transferase, wherein the nucleic acid can selectively hybridize to a DNA with a SEQ ID NO: 1 sequence. For example, the nucleic acid can selectively hybridize to a DNA with a SEQ ID NO: 1 sequence under stringent hybridization conditions. In some embodiments, the stringent hybridization conditions comprise a wash in 0.1×SSC, 0.1% SDS at 65° C. Such an isolated nucleic acid, which selectively hybridizes to a DNA with a SEQ ID NO: 1 sequence, can have at least about 90% sequence identity with SEQ ID NO: 1. In some embodiments, the isolated nucleic acid encoding a feruloyl-CoA:monolignol transferase has the SEQ ID NO: 1 sequence. Moreover, the nucleic acid encodes a feruloyl-CoA:monolignol transferase that, for example, can catalyze the synthesis of monolignol ferulate(s) from monolignol(s) and feruloyl-CoA. For example, the monolignol can be coniferyl alcohol, p-coumaryl alcohol, sinapyl alcohol or a combination thereof, and the feruloyl-CoA:monolignol transferase can, for example, synthesize coniferyl ferulate, p-coumaryl ferulate, sinapyl ferulate or a combination thereof.

As described in more detail herein, the feruloyl-CoA:monolignol transferase nucleic acids and polypeptides produce monolignol ferulates, which can be used for making plants that contain a readily cleavable lignin. In some embodiments, the feruloyl-CoA:monolignol transferase nucleic acid encodes a feruloyl-CoA:monolignol transferase polypeptide with a SEQ ID NO:2 sequence. In other embodiments, the nucleic acids can, for example, encode a feruloyl-CoA:monolignol transferase that can catalyze the synthesis of monolignol ferulate(s) from a monolignol(s) and feruloyl-CoA with at least about 50%, of the activity of a feruloyl-CoA:monolignol transferase with the SEQ ID NO:2.

Another aspect of the invention is a transgenic plant cell comprising an isolated nucleic acid encoding a feruloyl-CoA:monolignol transferase. The nucleic acid can include any of the feruloyl-CoA:monolignol transferase nucleic acids, as well as any of the nucleic acids described herein can selectively hybridize to a DNA with a SEQ ID NO: 1 sequence.

Another aspect of the invention is an expression cassette comprising one of the feruloyl-CoA:monolignol transferase nucleic acids described herein that is operably linked to a promoter functional in a host cell. Such a nucleic acid includes a nucleic acid that can selectively hybridize to a DNA with a SEQ ID NO: 1 sequence. The expression cassette can further comprise a selectable marker gene. In some embodiments, the expression cassette further comprises plasmid DNA. For example, the expression cassette can be within an expression vector. Promoters that can be used within such expression cassettes include promoters functional during plant development or growth.

Another aspect of the invention is a plant cell that includes an expression cassette comprising one of the feruloyl-CoA:monolignol transferase nucleic acids described herein that is operably linked to a promoter functional in a host cell. Such a plant cell can be a monocot cell. The plant cell can also be the plant is a gymnosperm cell. For example, the plant cell can be a maize, grass or softwood cell. In some embodiments, the plant cell is a dicot cell. For example, the plant cell can be a hardwood cell.

Another aspect of the invention is a plant that includes an expression cassette comprising one of the feruloyl-CoA:monolignol transferase nucleic acids described herein that is operably linked to a promoter functional in a host cell. Such a plant can be a monocot. The plant can also be a gymnosperm. For example, the plant can be a maize, grass or softwood plant. In some embodiments, the plant is a dicot plant. For example, the plant can be a hardwood plant.

Another aspect of the invention is a method for incorporating monolignol ferulates into lignin of a plant that includes:

a) stably transforming plant cells with the expression cassette comprising one of the feruloyl-CoA:monolignol transferase nucleic acids described herein to generate transformed plant cells;

b) regenerating the transformed plant cells into at least one transgenic plant, wherein feruloyl-CoA:monolignol transferase is expressed in at least one transgenic plant in an amount sufficient to incorporate monolignol ferulates into the lignin of the transgenic plant.

For example, such a method can be used to generate a transgenic plant that is fertile. The method can further include recovering transgenic seeds from the transgenic plant, wherein the transgenic seeds include the nucleic acid encoding a feruloyl-CoA:monolignol transferase. Such a plant can be a monocot. The plant can also be a gymnosperm. For example, the plant can be a maize, grass or softwood plant. In some embodiments, the plant is a dicot plant. For example, the plant can also be a hardwood plant. Such a method can further include stably transforming the plant cell(s) or the plant with at least one selectable marker gene. The selectable marker can be linked or associated with the expression cassette.

In some embodiments, the lignin in the plant that has the nucleic acid encoding a feruloyl-CoA:monolignol transferase can include at least 1% monolignol ferulate. In other embodiments, the lignin in the plant can include at least 5% monolignol ferulate, or at least 10% monolignol ferulate, or at least 20% monolignol ferulate, or at least 25% monolignol ferulate. In further embodiments, the lignin in the plant includes about 1-30% monolignol ferulate, or about 2-30% monolignol ferulate.

The method for incorporating monolignol ferulates into lignin of a plant can also include breeding the fertile transgenic plant to yield a progeny plant, where the progeny plant has an increase in the percentage of monolignol ferulates in the lignin of the progeny plant relative to the corresponding untransformed plant.

Another aspect of the invention is a lignin isolated from the transgenic plant comprising any of the feruloyl-CoA: monolignol transferase isolated nucleic acids described herein.

Another aspect of the invention is a method of making a product from a transgenic plant comprising: (a) providing a transgenic plant that includes one of the isolated nucleic acids described herein that encodes a feruloyl-CoA:monolignol transferase; and (b) processing the transgenic plant's tissues under conditions sufficient to digest to the lignin; to thereby generate the product from the transgenic plant, wherein the transgenic plant's tissues comprise lignin having an increased percent of monolignol ferulates relative to a corresponding untransformed plant. Such a corresponding untransformed plant is typically a plant of the same species, strain and/or accession as the transformed plant. The conditions sufficient to digest to the lignin can include conditions sufficient to cleave ester bonds within monolignol ferulate-containing lignin. In some embodiments, the conditions sufficient to digest to the lignin include mildly alkaline conditions. In some embodiments, the conditions sufficient to digest to the lignin include contacting the transgenic plant's tissues with ammonia for a time and a temperature sufficient to cleave ester bonds within monolignol ferulate-containing lignin. In some embodiments, the conditions sufficient to digest to the lignin would not cleave substantially any of the ether and carbon-carbon bonds in lignin from a corresponding plant that does not contain the isolated nucleic acid encoding the feruloyl-CoA:monolignol transferase.

Therefore, the invention embraces nucleic acid encoding a feruloyl-CoA:monolignol transferase and feruloyl-CoA: monolignol transferase enzymes, as well as expression cassettes, plant cells and plants that have such nucleic acids and enzymes, and methods of making and using such nucleic acids, polypeptides, expression cassettes, cells and plants.

DESCRIPTION OF THE DRAWINGS

FIGS. 1A1, 1A2, 1B1 and 1B2 illustrate structural models for some types of lignin polymers. FIGS. 1A1 and 1A2 show examples of lignin structures with 25 units that may be found in a softwood (spruce). FIGS. 1B1 and 1B2 show examples of lignin structures with 20 units that may be present in a hardwood (poplar). [Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK]. The softwood lignin is generally more branched and contains a lower proportion of β-ether units. Note that each of these structures represents only one of billions of possible isomers [Ralph, J., Lundquist, K., Brunow, G., Lu. F., Kim, H., Schatz, P. F., Marita, J. M., Hatfield, R. D., Ralph, S. A., Christensen, J. H., and Boerjan, W. Lignins: natural polymers from oxidative coupling of 4-hydroxyphenylpropanoids. (2004) *Phylochem. Revs.* 3(1), 29-60]. Thus, these structures are merely illustrative of some of the linkage types that may be present different lignins. An "S" within a ring indicates a syringyl unit while a "G" within a unit indicates a guaiacyl unit.

FIG. 2A is a no enzyme control assay while FIG. 2B shows the HPLC-separated assay results when the feruloyl-CoA:monolignol transferase enzyme from *Angelica sinensis* is present in the assay mixture. The peaks are numbered to distinguish the separated components of the assay as follows: 1) coniferyl alcohol (at about 4.4 min); 2) feruloyl-CoA (at about 5.4 min); 3) ferulic acid (about 6.0 min); and 4) coniferyl ferulate (at about 9.8 min)

FIG. 3A shows the assigned proton NMR spectrum of the product isolated from a reaction of coniferyl alcohol and feruloyl-CoA using the feruloyl-CoA:monolignol transferase from *Angelica sinensis*. FIG. 3B is a 2D $^1$H—$^3$C correlation (HSQC) spectrum of the same produced coniferyl ferulate, further authenticating the product; the tabulated $^{13}$C NMR data are from the 1D $^1$H-$^{13}$C NMR spectrum with the quaternary (non-protonated) carbons assigned by long-range $^1$H-$^{13}$C correlation (HMBC) spectra (not shown). These spectra (and proton and carbon data) match those from authentic (synthesized) coniferyl ferulate.

FIG. 4A shows the results of a no-enzyme control assay while FIG. 4B shows the results of the assay with the feruloyl-CoA:monolignol transferase from *Angelica sinensis*. The peaks are numbered to distinguish the separated components of the assay as follows: 1) p-coumaryl alcohol (at about 3.5 min), 2) feruloyl-CoA (at about 5.5 min), and 3) p-coumaryl ferulate (at about 9.0 min).

FIG. 5A shows the results of a no-enzyme control assay while FIG. 5B shows the results of the assay with the feruloyl-CoA:monolignol transferase from *Angelica sinensis*. The peaks are numbered to distinguish the separated components of the assay as follows: 1) sinapyl alcohol (at about 4.4 min); 2) feruloyl-CoA (at about 5.5 min); and 3) sinapyl ferulate (at about 9.4 min).

FIG. 6A shows the results of a no-enzyme control assay while FIG. 6B shows the results of the assay with the feruloyl-CoA:monolignol transferase from *Angelica sinensis*. The peaks are numbered to distinguish the separated components of the assay as follows: 1) coniferyl alcohol and p-coumaroyl-CoA (at about 4.4 min), the overlapping peaks cause a slight UV 280 asymmetry due to the coniferyl alcohol elution only slightly before the p-coumaroyl-CoA: and 3) coniferyl p-coumarate (at about 9.4 min).

FIG. 7A-7B shows HPLC separation of assay components where the assay was for feruloyl-CoA:monolignol transferase (FMT) activity using caffeoyl-CoA and coniferyl alcohol as substrates. The UV 340 trace is the dashed line while the UV 280 trace is the solid line. FIG. 6A shows the results of a no-enzyme control assay while FIG. 6B shows the results of the assay with the feruloyl-CoA:monolignol transferase from *Angelica sinensis*. The peaks are numbered to distinguish the separated components of the assay as follows: 1) coniferyl alcohol (at about 4.4 min); and 2) caffeoyl-CoA (at about 2.4 min).

FIG. 10A illustrates GFP-trap Mag enrichment and detection of FMT expression in the leaves of transgenic poplar trees that express FMT that has been N-terminally tagged with Yellow Fluorescent Protein (YFP-FMT). A western blot is shown of electrophoretically separated fractions obtained after GFPtrap (Chromotek) enrichment of YFP-FMT from the leaves of the transgenic poplar trees that express YFP-FMT. The FMT9 and FMT13 lanes contain extracts from two different genetically modified Poplar trees. FMT expression was detected using anti-GFP antibodies (Abcam). FIG. 10B illustrates the results obtained from a poplar leaf extract FMT enzyme assay. UPLC traces are of control and transgenic Poplar leaf extracts, where the transgenic Poplar trees express the YFP-FMT from *Angelica sinensis*. The absorbance of the substrates coniferyl alcohol (1) and feruloyl-CoA (2) are shown along with the FMT product, coniferyl ferulate (3), was detected at 280 nm (solid line) and 340 nm (dotted line). The top panel shows results obtained for wild-type Poplar leaf extracts (containing no *Angelica sinensis* FMT nucleic acids) while the bottom panel shows results obtained from extracts of transgenic poplar leaves that express the *Angelica sinensis* FMT. Coniferyl ferulate (3) was detected only with the leaf extract from YFP-FMT Poplar.

FIG. 11A illustrates the products of Reverse Transcriptase PCR that were amplified from *Arabidopsis* leaves transformed with empty vector or with a vector expressing the FMT transcript, when reverse transcriptase is added (+RT) or not added (−RT) to the PCR reaction mixture. A PCR product of the expected size for FMT (1326 base pairs) is visible only in the reaction containing total RNA from *Arabidopsis* transformed with the *Angelica sinensis* FMT when the reverse transcriptase is present. FIG. 11B provides representative UPLC traces showing FMT activity in ground stems from *Arabidopsis* transformed with the FMT from *Angelica sinensis*, when the FMT enzyme assay is employed (bottom panel). The absorbance for each of the substrates, coniferyl alcohol (1) and feruloyl-CoA (2) and for the product, coniferyl ferulate (3), was measured at 280 nm (solid line) and 340 nm (dotted line). Control reactions were conducted with stems expressing empty vector (top panel). Coniferyl ferulate (3) is detected only when protein from the transformed *Arabidopsis*-FMT stems was added.

Figure 2A:
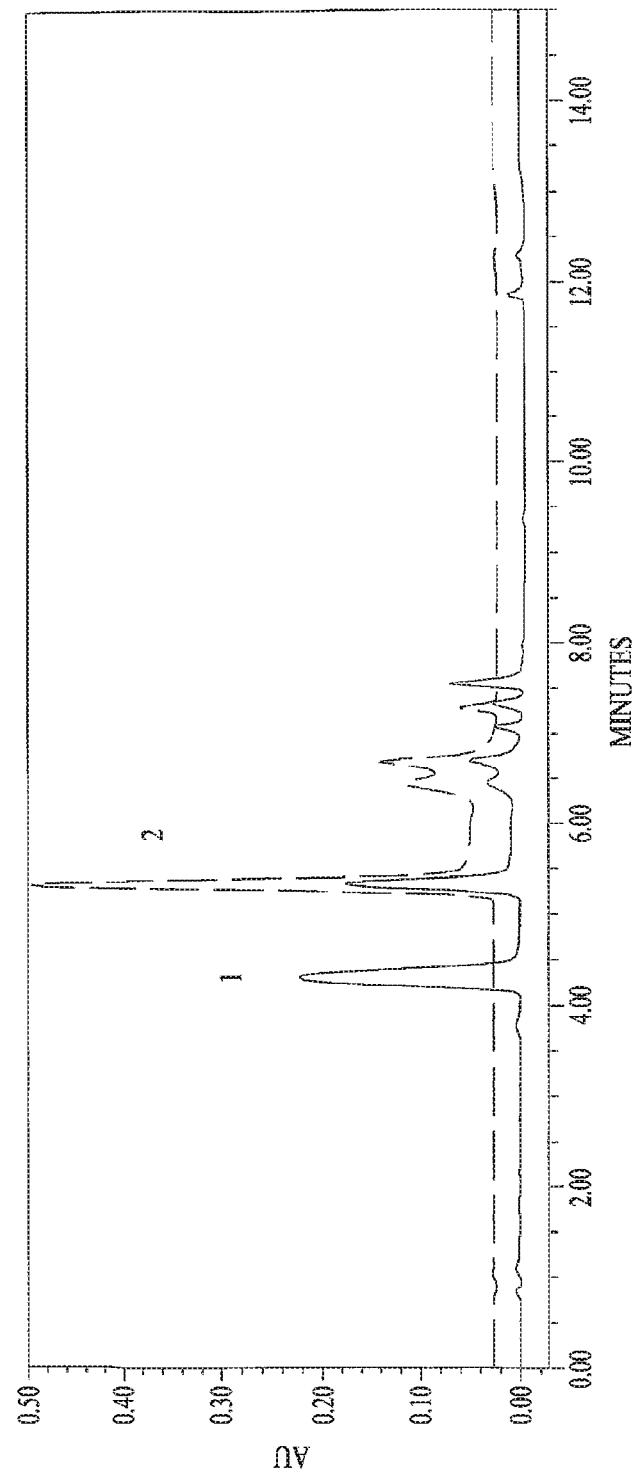
FIG. 2A-2B show HPLC traces of assay mixtures generated to test for feruloyl-CoA:monolignol transferase activity using coniferyl alcohol and feruloyl-CoA as substrates. The UV 340 trace is the dashed line while the UV 280 trace is the solid line.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

DETAILED DESCRIPTION OF THE INVENTION

The invention provides nucleic acids and methods useful for altering lignin structure and/or the lignin content in plants. Plants with such altered lignin structure/content are more easily and economically processed into useful products such as biofuels and paper.

Acyl-CoA Dependent Acyltransferases

Plant acyl-CoA dependent acyltransferases constitute a large but specific protein superfamily, named BAHD. Members of this family take an activated carboxylic acid (i.e., a CoA thioester form of the acid) as an acyl donor and either an alcohol or, more rarely, a primary amine, as an acyl acceptor and catalyze the formation of an ester or an amide bond, respectively. The acyl donors and acyl acceptors that act as substrates by BAHD acyltransferases are quite diverse, and different BAHD family members exhibit a range of substrate specificities.

The invention relates to a new class of BAHD acyltransferase nucleic acids and enzymes that enable the production of transgenic plants with altered lignin. The acyltransferases described herein are feruloyl-CoA:monolignol transferases that synthesize monolignol ferulates from any of three monolignols (p-coumaryl, coniferyl and sinapyl alcohols). For example, the feruloyl-CoA:monolignol transferases described herein can synthesize coniferyl ferulate from coniferyl alcohol and feruloyl-CoA, as shown below.

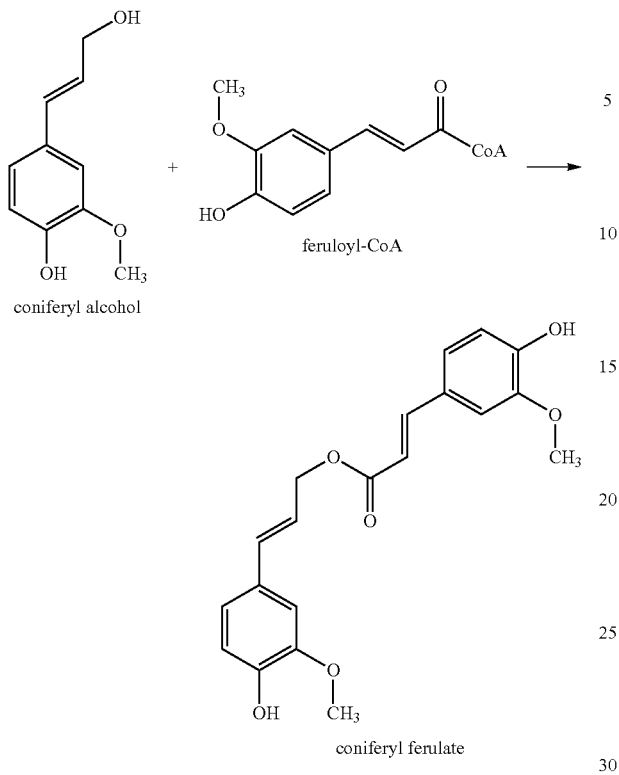

coniferyl alcohol + feruloyl-CoA → coniferyl ferulate

The feruloyl-CoA:monolignol transferases enable production of plants with lignin that is readily cleaved and/or removed, for example, because the lignin in these plants contains monolignol ferulates such as coniferyl ferulate (CAFA).

The terms "feruloyl-CoA:monolignol transferase(s)" and "monolignol ferulate transferase(s)" are used interchangeably herein.

Nucleic acids encoding the feruloyl-CoA:monolignol transferases that are useful for making coniferyl ferulate (and other monolignol ferulates) were isolated from the roots of *Angelica sinensis* as clone Dq155 pdest17. The coding region of the *Angelica sinensis* clone Dq155 pdest17 has the following nucleic acid sequence (SEQ ID NO: 1).

```
  1 ATGACGATCA TGGAGGTTCA AGTTGTATCT AAGAAGATGG
 41 TAAAGCCATC AGTTCCGACT CCTGACCACC ACAAGACTTG
 81 CAAATTGACG GCATTCGATC AGATTGCTCC TCCGGATCAA
121 GTTCCCATTA TTTACTTCTA CAACAGCAGC AACATCCACA
161 ATATTCGCGA GCAATTGGTA AAATCCTTGT CCGAAACTCT
201 AACCAAGTTT TATCCATTAG CTGGAAGATT TGTTCAAGAT
241 GGTTTCTATG TCGATTGTAA TGATGAAGGG GTCTTGTACG
281 TAGAAGCTGA AGTTAACATT CCGCTAAACG AATTCATCGG
321 ACAAGCAAAG AAAAATATAC AACTTATCAA TGATCTTGTT
361 CCGAAAAAAA ACTTCAAGGA TATTCATTCA TATGAAAATC
401 CAATAGTGGG ATTACAGATG AGTTATTCA AGTGTGGTGG
441 ACTTGCTATT TGCATGTATC TTTCGCATGT TGTAGCTGAT
481 GGATATACAG CAGCAGCATT CACTAAAGAG TGGTCTAACA
521 CAACCAATGG CATCATCAAT GGCGATCAAC TAGTTTCTTC
561 TTCTCCGATT AACTTCGAAT TGGCAACTCT AGTCCCAGCT
601 AGAGATTTAT CGACGGTGAT CAAGCCAGCC GTGATGCCAC
641 CATCAAAGAT CAAGGAAACC AAGGTTGTCA CAAGGAGGTT
681 TCTGTTCGAT GAAAATGCGA TATCAGCTTT CAAAGACCAT
721 GTCATCAAAT CCGAAAGCGT TAACCGGCCT ACACGGGTGG
761 AAGTTGTGAC ATCTGTGTTA TGGAAGGCTC TGATCAACCA
801 GTCTAAGCTT CCAAGTTCTA CACTATATTT TCACCTCAAC
841 TTTAGAGGGA AAACAGGCAT CAACACCCCA CCGCTAGATA
881 ATCATTTTTC GCTTTGCGGA AACTTTTACA CTCAGGTTCC
921 TACAAGGTTC AGGGGGGGAA ATCAAACAAA ACAGGATTTG
961 GAATTGCATG AATTGGTCAA GTTGTTGAGA GGAAAGTTGC
1001 GTAACACTCT GAAGAATTGC TCCGAAATTA ACACTGCCGA
1041 TGGGCTGTTC CTGGAAGCAG CTAGTAATTT CAATATTATA
1081 CAGGAAGATT TGGAGGACGA ACAAGTGGAT GTTCGGATTT
1121 TTACAACGTT GTGTAGGATG CCTTTGTATG AAACTGAGTT
1161 TGGGIGGGGA AAACCAGAAT GGGTTACCAT TCCAGAGATG
1201 CATTTGGAGA TAGTGTTTCT TTTGGACACT AAATGTGGGA
1241 CTGGTATTGA GGCATTAGTG AGCATGGATG AAGCAGATAT
1281 GCTTCAGTTT GAACTTGATC CCACCATCTC TGCTTTCGCT
1321 TCCTAG
```

The SEQ ID NO: 1 nucleic acid encodes a feruloyl-CoA:monolignol transferase enzyme with the following amino acid sequence (SEQ ID NO:2).

```
  1 MTIMEVQVVS KKMVKPSVPT PDHHKTCKLT AFDQIAPPDQ
 41 VPIIYFYNSS NIHNIREQLV KSLSETLTKF YPLAGREVQD
 81 GFYVDCNDEG VLYVEAEVNI PLNEFIGQAK KNIQLINDLV
121 PKKNFKDIHS YENPIVGLQM SYFKCGGLAI CMYLSHVVAD
161 GYTAAAFTKE WSNTTNGIIN GDQLVSSSPI NFELATLVPA
201 RDLSTVIKPA VMPPSKIKET KVVTRRFLFD ENAISAFKDH
241 VIKSESVNRP TRVEVVTSVL WKALINQSKL PSSTLYFHLN
281 FRGKTGINTP PLDNHFSLCG NFYTQVPTRF RGGNQTKQDL
321 ELHELVKLLR GKLRNTLKNC SEINTADGLF LEAASNFNII
361 QEDLEDEQVD VRIFTTLCRM PLYETEFGWG KPEWVTIPEM
401 HLEIVFLLDT KCGTGIEALV SMDEADMLQF ELDPTISAFA
441 S
```

The sequence of this new class of BAHD acyltransferases also allows identification and isolation of related nucleic acids and their encoded enzymes that also provide a means for production of altered lignins in plants.

For example, related nucleic acids can be isolated and identified by mutation of the SEQ ID NO: 1 sequence and/or by hybridization to DNA and/or RNA isolated from other plant species using SEQ ID NO:1 nucleic acids as probes. The sequence of the feruloyl-CoA:monolignol transferase enzyme (e.g., SEQ ID NO:2) can also be examined and used as a basis for designing alternative feruloyl-CoA:monolignol transferase nucleic acids that encode related feruloyl-CoA:monolignol transferase polypeptides.

In one embodiment, the BAHD acyltransferase nucleic acids of the invention include any nucleic acid that can selectively hybridize to SEQ ID NO:1.

The term "selectively hybridize" includes hybridization, under stringent hybridization conditions, of a nucleic acid sequence to a specified nucleic acid target sequence (e.g., SEQ ID NO: 1) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, or 60-90% sequence identity, or 90-95% sequence identity, or 90-99% sequence identity, or 95-97% sequence identity, or 98-99% sequence identity, or 100% sequence identity (or complementarity) with each other. In some embodiments, a selectively hybridizing sequence has about at least about 90% sequence identity or complementarity with SEQ ID NO: 1.

Thus, the nucleic acids of the invention include those with about 500 of the same nucleotides as SEQ ID NO: 1, or about 600 of the same nucleotides as SEQ ID NO: 1, or about 700 of the same nucleotides as SEQ ID NO: 1, or about 800 of the same nucleotides as SEQ ID NO: 1, or about 900 of the same nucleotides as SEQ ID NO: 1, or about 1000 of the same nucleotides as SEQ ID NO: 1, or about 1100 of the same nucleotides as SEQ ID NO:1, or about 1200 of the same nucleotides as SEQ ID NO: 1, or about 1300 of the same nucleotides as SEQ ID NO: 1, or about 500-1325 of the same nucleotides as SEQ ID NO:1. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., or 90-99% sequence identity, what is meant is that the value can be any integer between 90 and 99 inclusive, i.e., 90, 91, 92, 93, 94, 95, 96, 97, 98 or 99.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m = 81.5°\ C. + 16.6(\log M) + 0.41(\%\ GC) - 0.61(\%\ \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to SEQ ID NO: 1.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison (e.g., SEQ ID NO: 1 or 2). The reference sequence can be a nucleic acid sequence (e.g., SEQ ID NO: 1) or an amino acid sequence (e.g., SEQ ID NO:2). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson. et al., (1994) Meth. Mol. Biol. 24:307-31. An example of a good program to use for optimal global alignment of multiple sequences is PileUp (Feng and Doolittle, (1987) J. Mol. Evol. 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family. GAP displays four figures of merit for alignments: Quality. Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, with at least 55% sequence identity, preferably 60%, preferably 70%, preferably 80%, more preferably at least 90% or at least 95% sequence identity to the reference sequence over a specified comparison window. Optimal alignment may be ascertained or conducted using the homology alignment algorithm of Needleman and Wunsch, supra.

An indication that two polypeptide sequences are substantially identical is that both polypeptides have feruloyl-CoA:monolignol transferase activity, meaning that both polypeptides can synthesize monolignol ferulates from a monolignol and feruloyl-CoA. The polypeptide that is substantially identical to a feruloyl-CoA:monolignol transferase with a SEQ ID NO:2 sequence may not have exactly the same level of activity as the feruloyl-CoA:monolignol transferase with a SEQ ID NO:2. Instead, the substantially identical polypeptide may exhibit greater or lesser levels of feruloyl-CoA:monolignol transferase activity than the feruloyl-CoA:monolignol transferase with SEQ ID NO:2, as measured by assays available in the art or described herein (see, e.g., Example 1). For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the feruloyl-CoA:monolignol transferase with the SEQ ID NO:2 sequence when measured by similar assay procedures.

Alternatively, substantial identity is present when second polypeptide is immunologically reactive with antibodies raised against the first polypeptide (e.g., a polypeptide with SEQ ID NO:2). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The feruloyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a the SEQ ID NO:2 sequence. Alternatively, the feruloyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of a the SEQ ID NO:2 sequence.

Lignin

Lignin broadly refers to a biopolymer that is typically part of secondary cell walls in plants. Lignin is a complex moderately cross-linked aromatic polymer (see, e.g., FIG. 1). Lignin may also be covalently linked to hemicelluloses. Hemicellulose broadly refers to a class of branched sugar polymers composed of pentoses and hexoses. Hemicelluloses typically have an amorphous structure with up to hundreds or thousands of pentose units and they are generally at least partially soluble in dilute alkali. Cellulose broadly refers to an organic compound with the formula $(C_6H_{10}O_5)_z$ where z is an integer. Cellulose is a linear polysaccharide that can include linear chains of beta-1-4-linked glucose residues of several hundred to over ten thousand units.

Lignocellulosic biomass represents an abundant, inexpensive, and locally available feedstock for conversion to carbonaceous fuel (e.g., ethanol, biodiesel, biofuel and the like). However, the complex structure of lignin, which includes ether and carbon-carbon bonds that bind together the various subunits of lignin, and the crosslinking of lignin to other plant cell wall polymers, make it the most recalcitrant of plant polymers. Thus, significant quantities of lignin in a biomass can inhibit the efficient usage of plants as a source of fuels and other commercial products. Gaining access to the carbohydrate and polysaccharide polymers of plant cells for use as carbon and energy sources therefore requires significant energy input and often harsh chemical treatments, especially when significant amounts of lignin are present. For example, papermaking procedures in which lignin is removed from plant fibers by delignification reactions are typically expensive, can be polluting and generally require use of high temperatures and harsh chemicals largely because the structure of lignin is impervious to mild conditions. Plants with altered lignin structures that could be more readily cleaved under milder conditions would reduce the costs of papermaking and make the production of biofuels more competitive with currently existing procedures for producing oil and gas fuels.

Plants make lignin from a variety of subunits or monomers that are generally termed monolignols. Such primary monolignols include p-coumaryl alcohol, coniferyl alcohol, and sinapyl alcohol.

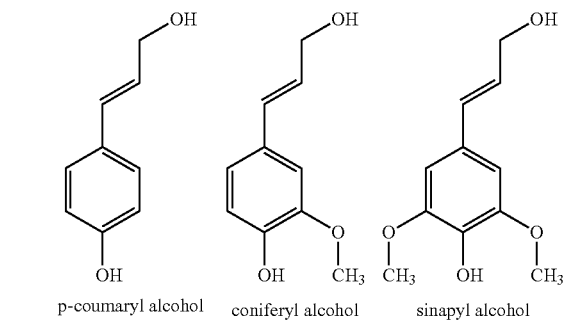

p-coumaryl alcohol    coniferyl alcohol    sinapyl alcohol

Monolignols destined for lignin polymerization in normal plants can be preacylated with acetate, p-hydroxybenzoate, or p-coumarate (Ralph et al., *Phytochem. Rev.* 3:29-60 (2004)). p-Coumarates acylate the γ-position of phenylpropanoid side chains mainly found in the syringyl units of lignin. Studies indicate that monolignols, primarily sinapyl alcohol, are enzymatically preacylated with p-coumarate prior to their incorporation into lignin, indicating that the monolignol p-coumarate conjugates, coniferyl p-coumarate and sinapyl p-coumarate, can also be 'monomer' precursors of lignin.

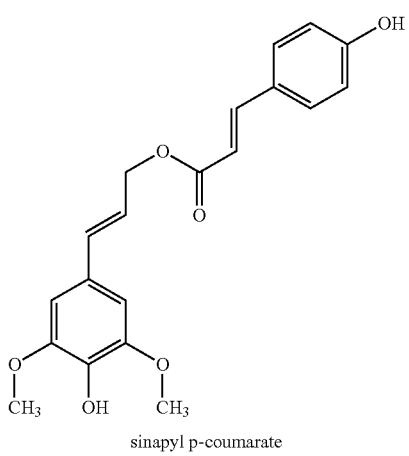 [SMILES: COc1cc(/C=C/COC(=O)/C=C/c2ccc(O)cc2)cc(OC)c1O]

sinapyl p-coumarate

While monolignol p-coumarate-derived units may comprise up to 40% of the lignin in some grass tissues, the p-coumarate moiety from such conjugates does not enter into the radical coupling (polymerization) reactions occurring during lignifications. Instead, the p-coumarate moieties substantially remain as terminal units with an unsaturated side chain and a free phenolic group (Ralph et al., *J. Am. Chem. Soc.* 116: 9448-9456 (1994); Hatfield et al., *J. Sci. Food Agric.* 79: 891-899 (1999)). Thus, the presence of sinapyl p-coumarate conjugates produces a lignin 'core' with terminal p-coumarate groups and no new bonds in the backbone of the lignin polymer, resulting in a lignin that is not significantly more easily cleaved.

In contrast to p-coumarate, ferulate esters do undergo radical coupling reactions under lignification conditions. Model ferulates, such as the ferulate shown below (where R is $CH_3$—, $CH_3$—$CH_2$—, a sugar, a polysaccharide, pectin, cell-wall (arabino)xylan or other plant component), readily undergo radical coupling reactions with each other and with lignin monomers and oligomers to form cross-linked networks.

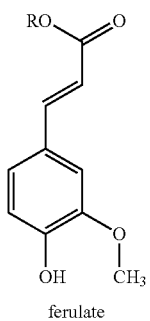

ferulate

If present during lignification, ferulates can become inextricably bound into the lignin by ether and C—C bonds. Although such ferulate moieties are no more extractable or cleavable from the lignin structure than other lignin units, the ester itself can be readily cleaved. Upon cleavage of such ester bonds, other plant cell wall components can be released. For example, an arabinoxylan (hemicellulose) chain can be released from a ferulate-mediated lignin attachment by cleaving the ester.

Ferulate-monolignol ester conjugates (unlike their p-coumarate analogs), such as coniferyl ferulate or sinapyl ferulate have not been identified in natural plant lignins, but some types of plants make them as secondary metabolites during, among other things, lignin biosynthesis. [Paula et al, *Tetrahedron* 51: 12453-12462 (1994); Seca et al., *Phytochemistry* 56: 759-767 (2001); Hsiao & Chiang, *Phytochemistry* 39: 899-902 (1995); Li et al., *Planta Med.* 72: 278-280 (2005)]. The structures of coniferyl ferulate and sinapyl ferulate are shown below.

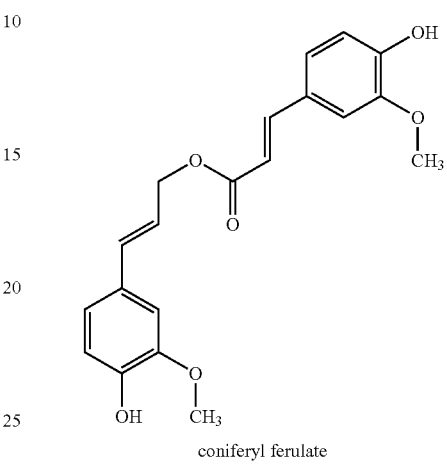

coniferyl ferulate

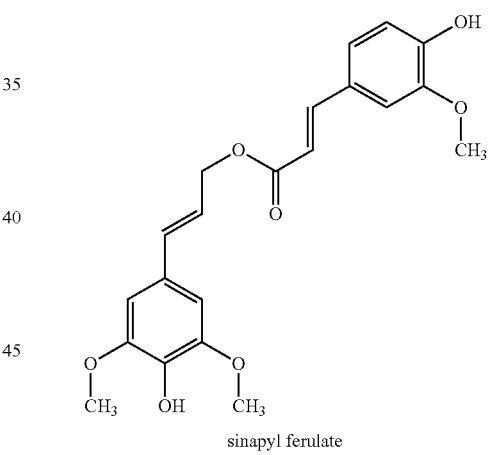

sinapyl ferulate

For example, the feruloyl-CoA:monolignol transferases provided herein biosynthesize coniferyl ferulate from coniferyl alcohol and feruloyl-CoA as shown below.

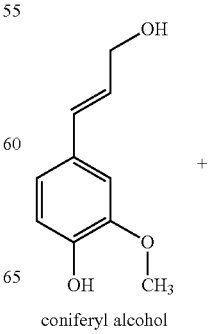

coniferyl alcohol

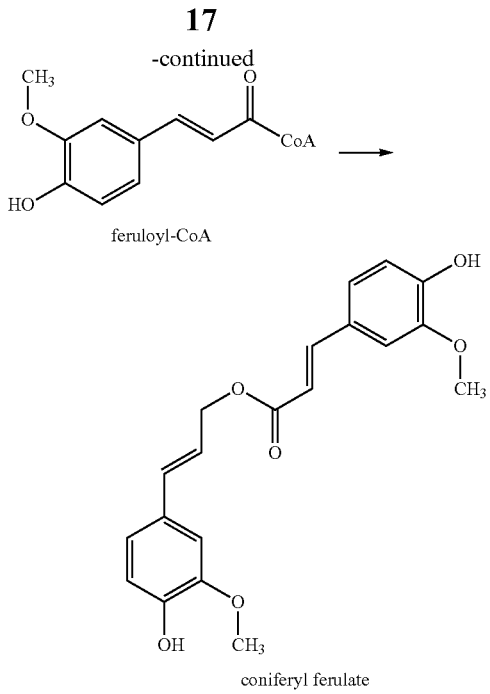

feruloyl-CoA coniferyl ferulate

The incorporation of monolignol ferulates into the lignin of plants allows the cell wall materials and lignin to be readily cleaved or processed into useful products. See also, U.S. Patent Application No. 61/213,706, the contents of which are specifically incorporated herein by reference in their entirety.

The monolignol ferulates made by the methods and feruloyl-CoA:monolignol transferases provided herein can be incorporated by radical coupling into plant lignins. Both the monolignol and the ferulate moieties can undergo such coupling, resulting in a lignin that can be complex. However, such 'double-ended-incorporation' still yields readily cleavable ester linkages that have been engineered into the backbone of the lignin polymer network. Esters are readily cleaved under much less stringent conditions by the same chemical processes used to cleave lignin, but the lignin resulting from the methods described herein is significantly easier to cleave, and provides more facile and less costly access to the plant cell wall polysaccharides. See also, "Method for modifying lignin structure using monolignol ferulate conjugates", U.S. Patent Application No. 61/213,706.

Lignins can be degraded by chemical or enzymatic means to yield a variety of smaller monomers and oligomers. While enzymatic processes are generally preferred because they do not require high temperatures and harsh chemicals, such enzymatic processes have previously not been as effective at solubilizing lignin moieties away from valuable plant cell constituents (e.g., polysaccharides and carbohydrates).

According to the invention, plants with the feruloyl-CoA:monolignol transferase nucleic acids and/or enzymes described herein supply monolignol ferulates for lignification in plants, thereby yielding plants with lignins that are more readily cleaved or processed to release cellulose, hemicelluloses and lignin breakdown products. Conditions for releasing the cellulose, hemicelluloses and lignin breakdown products from plants containing the feruloyl-CoA:monolignol transferase nucleic acids and/or enzymes described herein include conditions typically employed for cleaving ester bonds. Thus, the ester bonds within monolignol ferulate-rich lignins can be cleaved by milder alkaline and/or acidic conditions than the conditions typically used to break down the lignin of plants that are not rich in monolignol ferulates. For example, mildly alkaline conditions involving use of ammonia may be used to cleave the ester bonds within monolignol ferulate-rich lignins, whereas such conditions would not cleave substantially any of the ether and carbon-carbon bonds in normal lignins. See also, U.S. patent application Ser. No. 12/830,905, filed Jul. 6, 2010 and to U.S. Patent Application Ser. No. 61/213,706, filed Jul. 6, 2009, the contents of both of which are specifically incorporated herein by reference in their entireties.

Plants Modified to Contain a Feruloyl-CoA:Monolignol Transferase

In order to engineer plants with lignins that contain significant levels of monolignol ferulates, one of skill in the art can introduce feruloyl-CoA:monolignol transferases or nucleic acids encoding such feruloyl-CoA:monolignol transferases into the plants. For example, one of skill in the art could inject feruloyl-CoA:monolignol transferase enzymes into young plants. Alternatively, one of skill in the art can generate genetically-modified plants that contain nucleic acids encoding feruloyl-CoA:monolignol transferases within their somatic and/or germ cells. Such genetic modification can be accomplished by procedures available in the art. For example, one of skill in the art can prepare an expression cassette or expression vector that can express one or more encoded feruloyl-CoA:monolignol transferase enzymes. Plant cells can be transformed by the expression cassette or expression vector, and whole plants (and their seeds) can be generated from the plant cells that were successfully transformed with the feruloyl-CoA:monolignol transferase nucleic acids. Some procedures for making such genetically modified plants and their seeds are described below.

Promoters:

The feruloyl-CoA:monolignol transferase nucleic acids of the invention can be operably linked to a promoter, which provides for expression of mRNA from the feruloyl-CoA:monolignol transferase nucleic acids. The promoter is typically a promoter functional in plants and/or seeds, and can be a promoter functional during plant growth and development. A feruloyl-CoA:monolignol transferase nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but are not limited to, a plant promoter such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan. *Proc. Natl. Acad. Sci. USA.* 83:3320-3324 (1985). Other promoters useful in the practice of the invention are known to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A feruloyl-CoA:monolignol transferase nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The feruloyl-CoA:monolignol transferase nucleic acids can be subcloned downstream from the promoter using restriction enzymes and positioned to ensure that the DNA is inserted in proper orientation with respect to the promoter so that the DNA can be expressed as sense or antisense RNA. Once the feruloyl-CoA:monolignol transferase nucleic acid is operably linked to a promoter, the expression cassette so formed can be subcloned into a plasmid or other vector (e.g., an expression vector).

In some embodiments, a cDNA clone encoding a feruloyl-CoA:monolignol transferase protein is isolated from *Angelica sinensis* root tissue. In other embodiments, cDNA clones from other species (that encode a feruloyl-CoA: monolignol transferase protein) are isolated from selected plant tissues, or a nucleic acid encoding a mutant or modified feruloyl-CoA:monolignol transferase protein is prepared by available methods or as described herein. For example, the nucleic acid encoding a mutant or modified feruloyl-CoA:monolignol transferase protein can be any nucleic acid with a coding region that hybridizes to SEQ ID NO: 1 and that has feruloyl-CoA:monolignol transferase activity. Using restriction endonucleases, the entire coding sequence for the feruloyl-CoA:monolignol transferase is subcloned downstream of the promoter in a 5' to 3' sense orientation.

Targeting Sequences:

Additionally, expression cassettes can be constructed and employed to target the feruloyl-CoA:monolignol transferase nucleic acids to an intracellular compartment within plant cells or to direct an encoded protein to the extracellular environment. This can generally be achieved by joining a DNA sequence encoding a transit or signal peptide sequence to the coding sequence of the feruloyl-CoA:monolignol transferase nucleic acid. The resultant transit, or signal, peptide will transport the protein to a particular intracellular, or extracellular destination, respectively, and can then be posttranslationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences:

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the feruloyl-CoA:monolignol transferase nucleic acids by standard methods.

Selectable and Screenable Marker Sequences:

In order to improve identification of transformants, a selectable or screenable marker gene can be employed with the expressible feruloyl-CoA:monolignol transferase nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Example of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin. G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium. J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xy/E gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague. G. F. & Dudley, J. W. (*Am. Soc. Agron.*, Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology*. 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to substantially inhibit the translation of a mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay that measures the inhibition of translation of an mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

DNA Delivery of the DNA Molecules into Host Cells:

The present invention generally includes steps directed to introducing a feruloyl-CoA:monolignol transferase nucleic acids, such as a preselected cDNA encoding the selected feruloyl-CoA:monolignol transferase enzyme, into a recipient cell to create a transformed cell. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant species with lignin containing monolignol ferulates (e.g., coniferyl ferulate), wherein the plant has an introduced feruloyl-CoA: monolignol transferase nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include wheat, rice, *Arabidopsis*, tobacco, maize, soybean, and the like. In some embodiments, the plant or cell is a monocotyledon plant or cell. For example, the plant or cell can be a maize plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., *The Plant Cell*. 2:591-602 (1990)); direct DNA transfer to plant cells by PEG precipitation (Hayashimoto et al., *Plant Physiol*. 93:857-863 (1990)); direct DNA transfer to plant cells by microprojectile bombardment (McCabe et al., *Bio/Technology*. 6:923-926 (1988); Gordon-Kamm et al., *The Plant Cell*. 2:603-618 (1990); U.S. Pat. No. 5,489,520; U.S. Pat. No. 5,538,877; and U.S. Pat. No. 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. No. 5,384,253; and U.S. Pat. No. 5,472,869). For example, embryogenic cell lines derived from immature *Zea mays* embryos can be transformed by accelerated particle treatment as described by Gordon-Kamm et al. (*The Plant Cell*. 2:603-618 (1990)) or U.S. Pat. No. 5,489,520; U.S. Pat. No. 5,538,877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the feruloyl-CoA: monolignol transferase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., *PNAS*. 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell*. 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of a feruloyl-CoA:monolignol transferase nucleic acid to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the expressible feruloyl-CoA:monolignol transferase nucleic acids. In this case, one would then generally assay the potentially transformed cell population by exposing the cells to a selective agent or agents, or one would screen the cells for the desired marker gene trait.

Selection:

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue.

During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the feruloyl-CoA:monolignol transferase nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced feruloyl-CoA:monolignol transferase nucleic acids, the plant is self-pollinated at least once in order to produce a homozygous backcross converted inbred containing the feruloyl-CoA:monolignol transferase nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the feruloyl-CoA:monolignol transferase nucleic acids (or the feruloyl-CoA:monolignol transferase enzyme). Transgenic plant and/or seed tissue can be analyzed for feruloyl-CoA:monolignol transferase expression using standard methods such as SDS polyacrylamide gel electrophoresis, liquid chromatography (e.g., HPLC) or other means of detecting a product of feruloyl-CoA:monolignol transferase activity (e.g., coniferyl ferulate).

Once a transgenic seed expressing the feruloyl-CoA: monolignol transferase sequence and having an increase in monolignol ferulates in the lignin of the plant is identified, the seed can be used to develop true breeding plants. The true breeding plants are used to develop a line of plants with an increase in the percent of monolignol ferulates in the lignin of the plant while still maintaining other desirable functional agronomic traits. Adding the trait of increased monolignol ferulate production in the lignin of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of monolignol ferulates in the lignin of the plant. The resulting progeny are then crossed back to the parent that expresses the increased monolignol ferulate trait. The progeny from this cross will also segregate so that some of the progeny carry the trait and some do not. This back-crossing is repeated until an inbred line with the desirable functional agronomic traits, and with expression of the trait involving an increase in monolignol ferulates (e.g., coniferyl ferulate) within the lignin of the plant. Such expression of the increased percentage of monolignol ferulates in plant lignin can be expressed in a dominant fashion.

Subsequent to back-crossing, the new transgenic plants can be evaluated for an increase in the weight percent of monolignol ferulates incorporated into the lignin of the plant. This can be done, for example, by NMR analysis of whole plant cell walls (Kim, H., and Ralph, J. Solution-state 2D NMR of ball-milled plant cell wall gels in DMSO-$d_6$/pyridine-$d_5$. (2010) *Org. Biomol. Chem.* 8(3), 576-591; Yelle, D. J., Ralph, J., and Frihart, C. R. Characterization of non-derivatized plant cell walls using high-resolution solution-state NMR spectroscopy. (2008) *Magn. Reson. Chem.* 46(6), 508-517; Kim, H., Ralph, J., and Akiyama. T. Solution-state 2D NMR of Ball-milled Plant Cell Wall Gels in DMSO-$d_6$. (2008) *BioEnergy Research* 1(1), 56-66; Lu, F., and Ralph, J. Non-degradative dissolution and acetylation of ball-milled plant cell walls; high-resolution solution-state NMR. (2003) *Plant J.* 35(4), 535-544). The new transgenic plants can also be evaluated for a battery of functional agronomic characteristics such as lodging, kernel hardness, yield, resistance to disease and insect pests, drought resistance, and/or herbicide resistance.

Plants that may be improved by these methods include but are not limited to oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and *eucalyptus*). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues:

To confirm the presence of the feruloyl-CoA:monolignol transferase nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced feruloyl-CoA:monolignol transferase nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the feruloyl-CoA:monolignol transferase nucleic acid in question, they do not provide information as to whether the preselected DNA segment is being expressed. Expression may be evaluated by specifically identifying the protein products of the introduced feruloyl-CoA:monolignol transferase nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the feruloyl-CoA:monolignol transferase such as evaluation by amino acid sequencing following purification. The Examples of this application also provide assay procedures for detecting and quantifying feruloyl-CoA:monolignol transferase activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Definitions

As used herein. "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, a "native" nucleic acid or polypeptide means a DNA, RNA or amino acid sequence or segment that has not been manipulated in vitro, i.e., has not been isolated, purified, and/or amplified.

The following non-limiting Examples illustrate how aspects of the invention have been developed and can be made and used.

Example 1: Materials and Methods

This Example illustrates some methods that can be employed to make and use the invention.

*Angelica sinensis* Tissue Collection and Total RNA Extraction

One- and two-year-old field grown *Angelica sinensis* plants (Mountain Gardens Herbs), were transplanted into Readi-Earth and grown for two months in a greenhouse to recover. The single root of a two-year plant was harvested, cut into small pieces, and ground in liquid nitrogen to a fine powder. Total RNA was extracted by adding 100 mg of powdered *Angelica sinensis* root tissue to 1 ml Trizol buffer (Invitrogen) and incubating for 15 minutes while vortexing at room temperature. One-fifth volume of chloroform was added and incubated for an additional 15 minutes. After centrifugation at 15000×g for 35 minutes at 4° C., the aqueous phase was extracted with ⅕ volume of chloroform. Total RNA was precipitated from the aqueous phase by adding ⅕ volume of a solution containing 1 M sodium chloride and 0.8 M sodium citrate and ⅕ volume of isopropyl alcohol. The RNA was collected by centrifugation at 12,000×g and the pellet was washed in 70% ethanol, dried and dissolved in RNase-free water. Residual DNA was removed by DNase digestion using the RNase-free DNase Kit (Qiagen), following manufacturer's guidelines. RNA quality was assessed using an Agilent 2100 Bioanalyzer.

Library Quality cDNA Synthesis and 454 Sequencing

A cDNA library was constructed from *Angelica sinensis* root RNA using the Creator SMART cDNA Library Construction Kit (Clontech). First-strand cDNA was synthesized by combining 1 μg of RNA with 10 μM SMART IV Oligo, 10 μM of modified CDS III/3' cDNA synthesis primer 5'-TAG AGG CCG AGG CGG CCG ACA TGT TTT GTT TTT TTT TCT TTT TTT TTT VN-3' (SEQ ID NO:3) with PAGE purification (Integrated DNA Technologies), and deionized water to a final volume of 5 μL and incubated at 72° C. for 2 minutes. Samples were cooled on ice for 2 minutes and a solution of 2 μL 5× First Strand Buffer, 20 nM dithiothreitol (Creator SMART cDNA Library Construction Kit, Clontech), 10 nM dNTP mix and 200 units SuperScript II Reverse Transcriptase (Invitrogen) was added to each reaction tube. Samples were incubated at 42° C. for 1 hour, and then placed on ice to terminate first strand cDNA synthesis.

Double stranded cDNA was amplified from first strand cDNA synthesis reactions by combining 2 μL of first strand cDNA, 10 μL 10× Advantage 2 PCR Buffer (Advantage 2 Polymerase Mix, Clontech), 20 nM dNTP mix (Invitrogen), 20 pM 5' PCR Primer (Creater SMART cDNA Library Construction Kit, Clontech), 20 pM Modified CDS III/3' PCR Primer (IDT, see sequence above), 2 μL 50× Advantage 2 Polymerase Mix (Clontech), and deionized water to a final volume of 100 μL. This reaction was placed in a thermal cycler, preheated to 95° C., and cycled 24 times (95° C. for 1.25 minutes and 68° C. for 6 minutes). A 5 μL aliquot of each double stranded cDNA reaction was analyzed by gel electrophoresis. The cDNA was subjected to Proteinase K digestion by adding 40 μg of Proteinase K with incubation at 45° C. for 20 minutes. A solution of 50% phenol and 50% chloroform was used to extract proteins from each cDNA sample followed by two chloroform extraction. The double stranded cDNA was pooled from all reactions and precipitated by adding ⅒ volume of 3 M sodium acetate pH 4.8, 20 μg glycogen, and 2.5 volumes ethanol at room temperature. After centrifugation at 15000×g, the cDNA pellet was washed with 80% ethanol, dried and dissolved in 79 μL deionized water. The double stranded cDNA was digested with SfiI to remove concatenated primers and size fractionated using Chroma Spin+TE-1000 Columns (Clontech) to remove short fragments. Fractions were analyzed by agarose gel electrophoresis and the fractions with sizes above 500 base pairs were pooled. cDNA was submitted to the Genomics Core at Michigan State University for Roche 454 sequencing using the 454 GSFLX Titanium Sequencer.

Amplification and Cloning of Feruloyl-CoA:Monolignol Transferase (FMT)

cDNA was synthesized from the *Angelica sinensis* root total RNA, using Superscript III Reverse Transcriptase (Invitrogen). After DNase digestion, 5 µg of total RNA was added to 0.5 µg Oligo d(T)$_{12-18}$, 10 nM dNTP mix (Invitrogen) and DEPC water to a volume of 13 µL. The reaction mixture was incubated at 65° C. for 5 minutes. After cooling the sample on ice for 2 minutes, 4 µL of 5× First-strand Buffer, 100 nM DTT, 40 units RNase OUT and 200 units Superscript III Reverse Transcriptase (Invitrogen) were added and incubated at 50° C. for 60 minutes. The reaction was inactivated by heating to 70° C. for 15 minutes and stored on ice. The FMT coding sequence was amplified using 5'-AAA AAA GCA GGC TTC ATG ACG ATC ATG GAG GTT CAA GTT-3' (SEQ ID NO:4) and 5'-GTA CAA GAA AGC TGG GTT CTA GGA AGC GAA AGC AGA GAT-3' (SEQ ID NO:5) oligonucleotides (Integrated DNA Technologies) as forward and reverse gene specific primers with partial Gateway attB1 and attB2 attachment sites. Using the Platinum Pfx DNA Polymerase kit (Invitrogen), 2 µL 10× Pfx Amplification Buffer, 7.5 nM dNTP mix, 25 nM magnesium sulfate, 10 mM of each primer, 2.5 units of Plantinum Pfx DNA Polymerase and deionized water to a final volume of 20 µL was added to 200 ng cDNA. The sample was denatured at 94° C. for 4 minutes, followed by 25 cycles of 94° C. for 30 seconds, 55° C. for 30 seconds, 68° C. for 1 minute 45 seconds. After a cooling the sample to 4° C., a second PCR reaction was completed, as described above, using 5'-GGGG ACA AGT TTG TAC AAA AAA GCA GGC T-3' (SEQ ID NO:6) and 5'-GGG AC CAC TTT GTA CAA GAA AGC TGG GT-3' (SEQ ID NO:7) oligonucleotides (Integrated DNA Technologies) as forward and reverse primers and 2.5 µL of the first PCR reaction to add full length Gateway attB1 and attB2 attachment sites to the coding sequence. After amplification, the reaction was analyzed by electrophoresis on a 0.8% agarose gel and the PCR product was purified using the QIAquick Gel Extraction Kit (Qiagen), following manufacturer's guidelines.

The amplified FMT coding sequence was cloned into the Gateway entry vector pDONR221 (Invitrogen) using the BP Clonase II Enzyme Mix (Invitrogen). After purification, 150 ng of PCR product was added to 150 ng of pDONR221 entry vector, to a final volume of 4 µL with TE buffer, and 1 µL BP Clonase II Enzyme Mix. The reaction was incubated overnight at room temperature, inactivated by adding 1 µg Proteinase K and incubating at 37° C. for 10 minutes. After cooling on ice, 2.5 µL of the reaction was used to transform One Shot Top 10 Chemically Competent *E. coli* Cells (Invitrogen) according to manufacturer's guidelines. The transformants were grown at 37° C. overnight on LB agar plates containing and 50 µg/ml Kanamycin. Single colonies were picked and grown in LB media containing 50 µg/ml Kanamycin overnight at 37° C. Plasmid DNA was purified from these cultures using the QIAprep Spin Miniprep Kit (Qiagen), according to manufacturer's guidelines. Samples were submitted for high throughput sequencing, using the M13 forward and M13 reverse primers (Invitrogen) at the Michigan State University Genomics Core, and compared to the 454 sequencing data to verify coding sequence using DNASTAR Lasergene 8 software.

Sequences in entry vectors were inserted into pDEST17 vector using 150 ng of plasmid DNA from the entry clone, 150 ng of pDEST17 vector and 1 µL LR Clonase II Enzyme Mix. The reaction was incubated overnight at room temperature. Transformation of competent cells was completed as described above. Transformants were selected on LB agar plates containing 100 µg/ml Ampicillin. Clones were screened by PCR using Gotaq Hot Start Green Master Mix (Promega) by adding 10 µL of the 2× master mix to 10 mM of each gene specific primer, deionized water to final volume of 20 µL. This PCR reaction was denatured at 94° C. for 3 minutes then cycled 25 times through 94° C. for 30 seconds, 55° C. for 30 seconds, 72° C. for 1 minute 45 seconds, with a final elongation step at 72° C. for 5 minutes before cooling to 4° C. Each reaction was analyzed by gel electrophoresis. Clones were then transformed into One Shot BL21 Chemically Competent *E. coli* Cells (Invitrogen), according to manufacturer's guidelines, for expression.

Expression of Feruloyl-CoA:Monolignol Transferase (FMT) in *E. coli*

Cultures of BL21 *E. coli* containing FMT nucleic acids in the expression vector were grown at 37° C. overnight in 5 ml LB media containing 100 µg/ml ampicillin. The cultures were then added to 1 L of LB media containing 100 µg/ml ampicillin and grown to an OD600 of 0.4 to 0.5. Protein expression in the cells was induced by adding 1 mM of isopropyl β-D-1-thiogalactopyranoside (IPTG) and the cells were incubated for 6 hours at 22° C. Cells were harvested by centrifugation at 4° C. and pellets were stored at −80° C. The pellets were suspended in 10 ml of binding buffer, a solution containing 20 mM Tris-hydrochloride pH 8, 0.5 M sodium chloride, 1 mM 2-mercaptoethanol and cells were lysed using a French press. The extract was then centrifuged at 50,000×g for 30 minutes at 4° C. to separate soluble and insoluble protein fractions. The soluble protein fraction in the supernatant was collected and the insoluble protein fraction was suspended in 10 ml of suspension buffer. Both fractions were analyzed for expression on an SDS-PAGE gel.

Purification of *E. coli* Expressed Feruloyl-CoA:Monolignol Transferase (FMT)

HIS-tagged FMT was purified using an AKTA purifier (GE Healthcare) operated with UNICORN 5.11—workstation version (GE Healthcare) and a protocol modified from the manufacturer's guidelines. Four 5 ml HiTrap desalting columns (GE Healthcare) were equilibrated with binding buffer. A 5 ml aliquot of the soluble protein was injected onto the desalting column and eluted with binding buffer at a flow rate of 1 ml/minute. Fractions with the highest protein concentrations, as indicated by higher UV absorbance, were collected in 1 ml fractions. These fractions were applied to a 1 ml HisTrap HP column (GE Healthcare), conditioned and charged with 0.1 M NiSO$_4$, according to manufacturer's guidelines, at a flow rate of 0.1 ml/minute. The column was washed with 5 ml of buffer A (20 mM Tris-hydrochloride pH 8, 0.5 M sodium chloride, 1 mM 2-mercaptoethanol, and 20 mM imidazole) then bound protein was eluted at 1 ml/minute with a 20 ml linear gradient from buffer A to buffer B (20 mM Tris-hydrochloride pH 8, 0.5 M sodium chloride, 1 mM 2-mercaptoethanol, and 500 mM imidazole). Fractions containing protein were collected and analyzed by SDS-PAGE. Fractions with the highest concentration of FMT were combined and desalted using an Amicon Ultracel 10K membrane filter (Millipore).

Feruloyl-CoA:Monolignol Transferase (FMT) Enzymatic Assay

The feruloyl-CoA, p-coumaroyl-CoA, and caffeoyl-CoA substrates used in the FMT assay were enzymatically synthesized using the tobacco 4-coumarate-CoA-ligase (4CL)

with a c-terminal HIS tag in pCRT7/CT TOPO, provided by Eran Pichersky. Following a method modified from Beuerle and Pichersky (Anal. Biochem. 302(2): 305-12 (2001)) 3.3 mg of ferulic acid, coumaric acid or caffeic acid, 2 mg coenzyme A, and 6.9 mg ATP were added to 50 mM Tris-hydrochloride pH 8 and 2.5 mM magnesium chloride in a final volume of 10 ml. The reaction was started by adding 0.25 mg 4CL, protein purified as described by the method of Beurerle and Pichershy. After a five-hour incubation at room temperature, additional 6.9 mg ATP, 2 mg coenzyme A, and 0.25 mg purified 4CL were added and the reaction was incubated overnight. The CoA esters were purified on an SPE cartridge as described in Beuerle and Pichersky (2001).

The FMT activity assay contained 100 mM MOPS pH 6.8, 1 mM dithiothreitol (DTT), 1 mM feruloyl-CoA, 1 mM coniferyl alcohol, 3.9 µg of purified FMT protein and deionized water to a volume of 50 µL. After a 30-minute incubation, 1 µL of 10 M hydrochloric acid was added to stop the reaction. Because the product synthesized in the reaction, coniferyl ferulate (CAFA), is insoluble, 50 µL of methanol was added to solubilize the CAFA. Prior to UPLC, protein and insoluble material were removed by filtering through an Amicon Ultracel 10K membrane filter (Millipore). The flow-through was analyzed using an Acquity Ultra Performance LC with an Acquity UPLC BEH C18 1.7 µm 2.1×100 mm column and the Acquity Console and Empower 2 Software, all from Waters Corporation. The solvents used in this method were solvent A, 0.1% trifluoroacetic acid, and solvent B, 100% acetonitrile. Samples were analyzed using the following gradient conditions, 13% B, for 5 minutes, 1 minute linear gradient to 42% B, held for 4 minutes, 1 minute linear gradient to 100% B, held for 1 minutes and 3 minutes at 13% B with a flow rate of 0.3 ml/minute. This method was then used to analyze a 10 µL injection of each assay reaction; standards for each of the substrates along with chemically synthesized CAFA were used to determine retention times for each compound.

Size Exclusion Chromatography of FMT

A 100 µL sample of protein purified by immobilized metal ion affinity chromatography (IMAC) was loaded onto a Superdex 75 10/300 GL gel filtration column (GE Healthcare), equilibrated with 100 mM MOPS pH 6.8. The protein was eluted with the same buffer at a constant flow rate of 0.1 ml/minute and collected in 0.5 ml fractions. Aliquots of the protein sample prior to gel filtration, and each of the fractions near the elution peak were analyzed for protein content by SDS-PAGE gel electrophoresis. Protein containing fractions were analyzed to determine the amount of FMT activity, as described above.

NMR

Figure 3A:
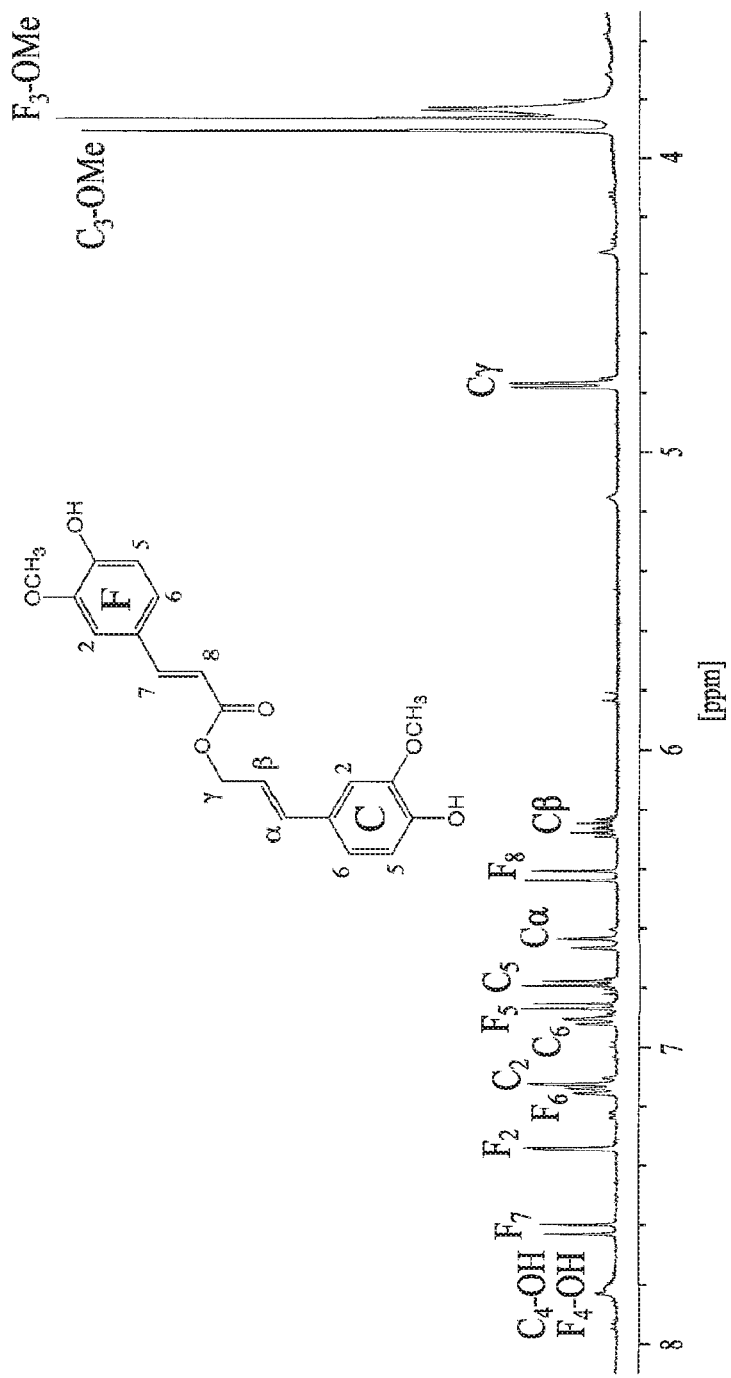
FIG. 3A-3B illustrate the NMR identification of coniferyl ferulate (CAFA).
Figure 3B:
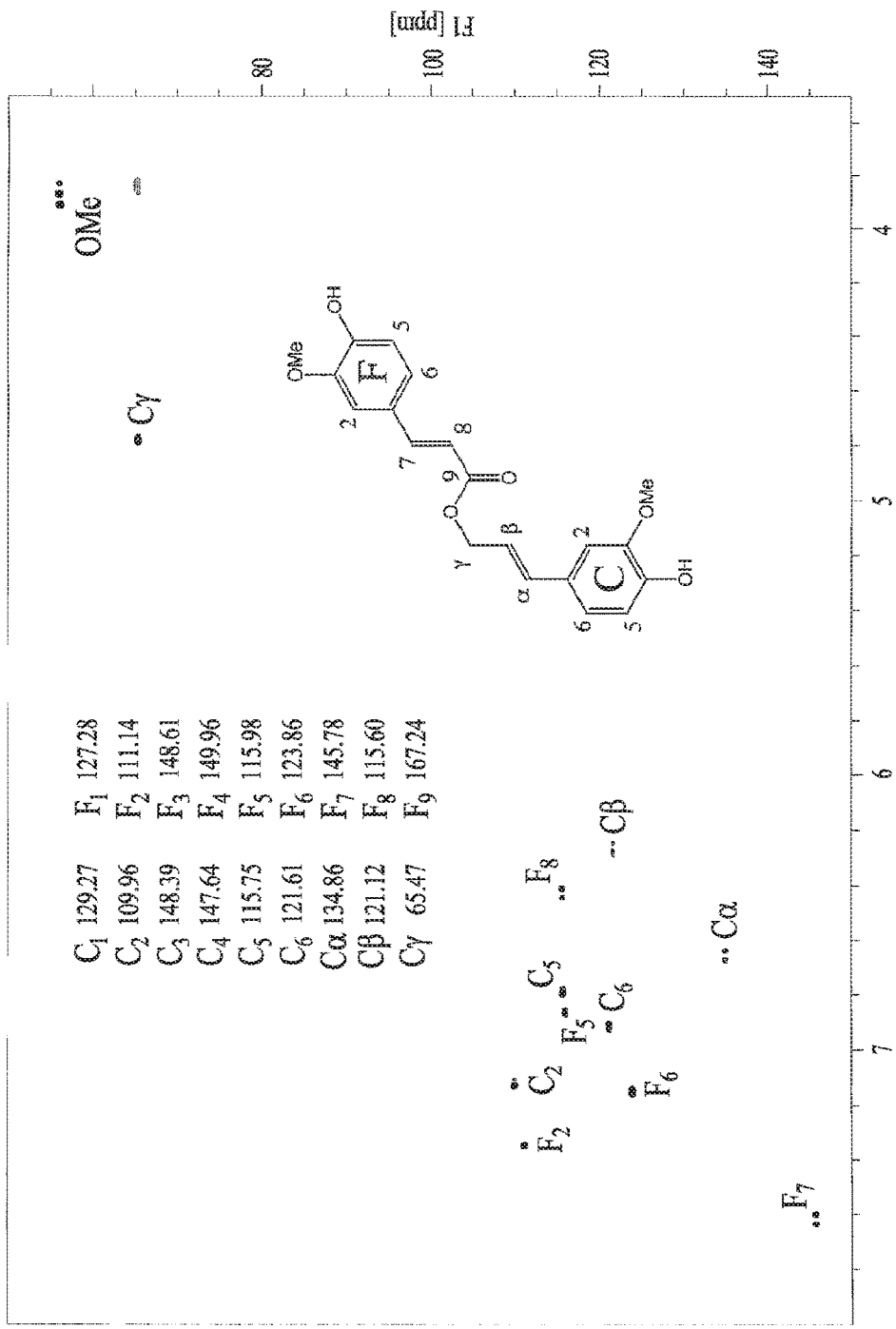

To confirm the identification based on the chromatogram peak comparisons, the reaction product, which was insoluble before addition of methanol, was centrifuged to pellet the coniferyl ferulate, which was dissolved in perdeuteroacetone and analyzed by NMR. The proton NMR spectrum, FIG. 3A, unambiguously confirmed the authenticity of the coniferyl ferulate product, particularly when compared with the spectrum from the independently synthesized coniferyl ferulate (described below). For absolute confirmation, $^{13}$C NMR data was also obtained via a 2D $^1$H-$^{13}$C correlation (HSQC) spectrum (for the protonated carbons, FIG. 3B) and a 2D $^1$H-$^{13}$C long-range correlation (HMBC) spectrum (not shown, but data for all carbons is given on FIG. 3B).

Synthesis of Authentic Coniferyl Ferulate

Figure 9:
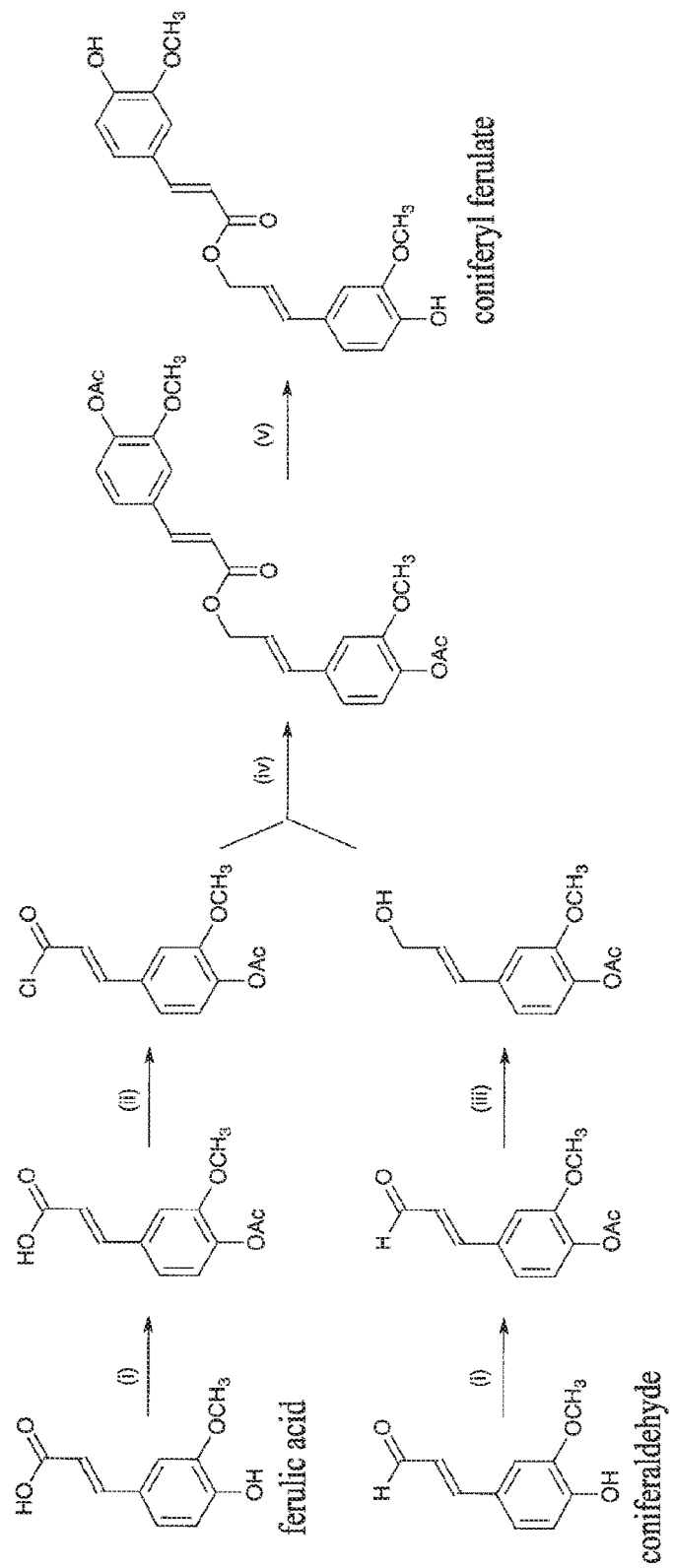
FIG. 9 illustrates the synthetic scheme used to prepare authentic coniferyl ferulate, employing (i) acetic anhydride, pyridine; (ii) thionyl chloride; (iii) borane/tert-butylamine; (iv) triethylamine, dimethylaminopyridine; and (v) pyrrolidine.

The synthesis was similar to that described for the related compound, coniferyl p-coumarate (Lu, F., and Ralph, J. Facile synthesis of 4-hydroxycinnamyl p-coumarates. (1998) *J. Agr. Food Chem.* 46(8), 2911-2913). Thus, as shown in FIG. 9, 4-acetoxyferuloyl chloride was prepared from ferulic acid by acetylation followed by chlorination using $SOCl_2$ according to a previous method (Helm, R. F., Ralph, J., and Hatfield, R. D. Synthesis of feruloylated and p-coumaroylated methyl glycosides. (1992) *Carbohydr. Res.* 229(1), 183-194).

4-Acetoxyconiferaldaldehyde was prepared in 94-96% yield by acetylation of coniferaldehyde with acetic anhydride/pyridine and then reduced with borane/tert-butylamine complex to give the corresponding alcohol, as follows. The 4-acetoxyconiferaldehyde was dissolved in methylene chloride to which borane/tert-butylamine complex (1.5 equiv) was added. The mixture was stirred at room temperature for 2 h, when TLC showed that the starting material had disappeared completely. The solvent was evaporated at 40° C. under reduced pressure. The residue was hydrolyzed with 0.5 M $H_2SO_4$ in ethanol/water (1:1) for 1.5 h. Most of the ethanol was removed by evaporation, and the product was extracted with ethyl acetate. The ethyl acetate solution was washed with saturated $NH_4Cl$ and dried over $MgSO_4$. Evaporation of the ethyl acetate gave the product, 4-acetoxyconiferyl alcohol as a pale yellow oil (96% yield); $^1$H NMR (acetone-$d_6$) δ 2.31 (3H, s, OAc), 3.83 (3H, s, OAc), 3.90 (1H, t, J) 5.5 Hz, γ-OH), 4.22 (2H, dr, J) 5.5, 1.7 Hz, γ), 6.38 (1H, dt, J) 15.9, 5.2 Hz, β), 6.58 (1H, dt, J=15.9, 1.7 Hz, α), 6.97 (2H, m, A5/6), 7.15 (s, 1H, A2); 13C NMR δ 20.5 (OAc), 56.2 (OMe), 63.1 (γ), 110.9 (A2), 119.5 (A6), 123.6 (A5), 129.3 (α), 131.4 (β), 137.2 (A1), 140.2 (A4), 152.3 (A3), 169.0 (OAc).

4-Acetoxyconiferylferulate.

Coupling of 4-acetoxyferuloyloyl chloride with 4-acetoxyconiferyl alcohol was efficiently carried out using 4-(dimethylamino)-pyridine (DMAP). Thus, 4-acetoxyconiferyl alcohol and 4-acetoxyferuloyl chloride were dissolved in dry $CH_2Cl_2$ (120 mL) to which DMAP (0.25 equiv) and $Et_3N$ (0.85 equiv) were added. The mixture was stirred for 2 h, when TLC [$CHCl_3$/EtOAc (5:1)] showed the starting material was converted into a faster moving compound. The solution was diluted with $CH_2Cl_2$ and washed successively with aqueous 3% HCl and saturated $NH_4Cl$. Drying over $MgSO_4$, evaporation, and purification by flash chromatography [$CHCl_3$/EtOAc (19:1)] gave the diacetate of coniferyl ferulate (94%) as a pale yellow oil.

Coniferyl Ferulate.

The above diacetate (0.195 mmol) was dissolved in pyrrolidine (1 mL). Once dissolution was complete, the pyrrolidine solution was diluted with 50 mL of ethyl acetate and washed with 1 M $H_2SO_4$ (3×20 mL) and saturated $NH_4Cl$ (2×20 mL). After drying over $MgSO_4$ and evaporation, the resulting syrup was submitted to solid phase extraction [$CHCl_3$/EtOAc (19:1)] to afford coniferyl ferulate (93%) as a white solid. NMR spectra are the same as those for the FMT-enzyme generated product, as shown in FIG. 3.

Example 2: Identification and Cloning of a Feruloyl-CoA:Monolignol Transferase

Mature *A. sinensis* plants were purchased from Mountains, Gardens and Herbs (North Carolina) and RNA was extracted from the roots of these plants. This RNA was used to synthesize double-stranded cDNA. The cDNA was sequenced using a Roche GSFLX Titanium Sequencer and 736,017 sequences were obtained. The sequences were assembled into 62425 contigs using CAP3 (Huang, X., A contig assembly program based on sensitive detection of fragment overlaps. (1992) *Genomics* 14: 18-25). The consensus sequence for each contig was searched against all proteins from *Arabidopsis* and the NCBI non-redundant protein databases using the BLASTX software program (Altschul S, Gish W, Miller W. Myers E. Lipman D. Basic local alignment search tool. (1990) *J Mol Biol* 215(3), 403-410). The sequences were sorted by abundance and filtered to show only sequences annotated as being within a "transferase family," which is the annotation in the TAIR9 database assigned to members of the BAHD class of acyltransferases.

Two very abundant BAHD acyltransferases were identified as well as a number of such enzymes with lower EST counts. These two sequences were cloned by PCR from an *A. sinensis* cDNA pool using oligonucleotides designed to amplify their coding regions. The coding region of the *A. sinensis* sequences was transferred to the expression vector pDEST17 using Gateway technology. This vector adds an amino-terminal 6xHIS-tag to the protein, which allows for affinity purification by immobilized metal affinity chromatography (IMAC). *E. coli* clones containing the recombinant protein where grown and induced to produce recombinant protein. The enzyme was purified from the *E. coli* protein extract using IMAC.

Figure 2B:
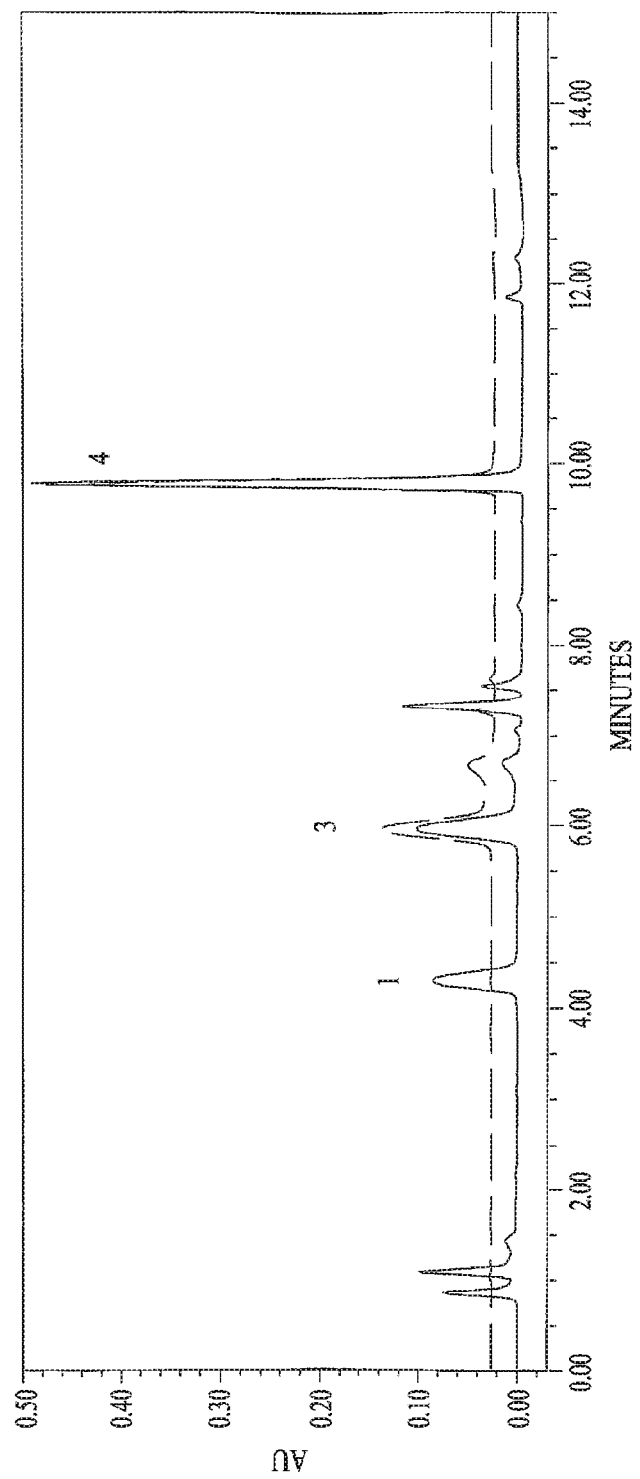

Purified recombinant enzyme was assayed for FMT activity using a reaction mixture containing 2 mM coniferyl alcohol, 0.5 feruloyl-CoA, 100 mM HEPES pH 7.4 and 1 mM DTT. The second most abundant BAHD acyltransferase gene when incubated with Coniferyl alcohol and feruloyl-CoA produced a compound with the retention time of authentic coniferyl ferulate (CAFA) (FIG. 2). The product produced was mostly insoluble in water. The addition of methanol to 50% after stopping the enzyme with acid was required to analyze the product by UPLC. The insolubility of the product made partial purification easy as the product was separated from the substrates by centrifugation.

Figure 4A:
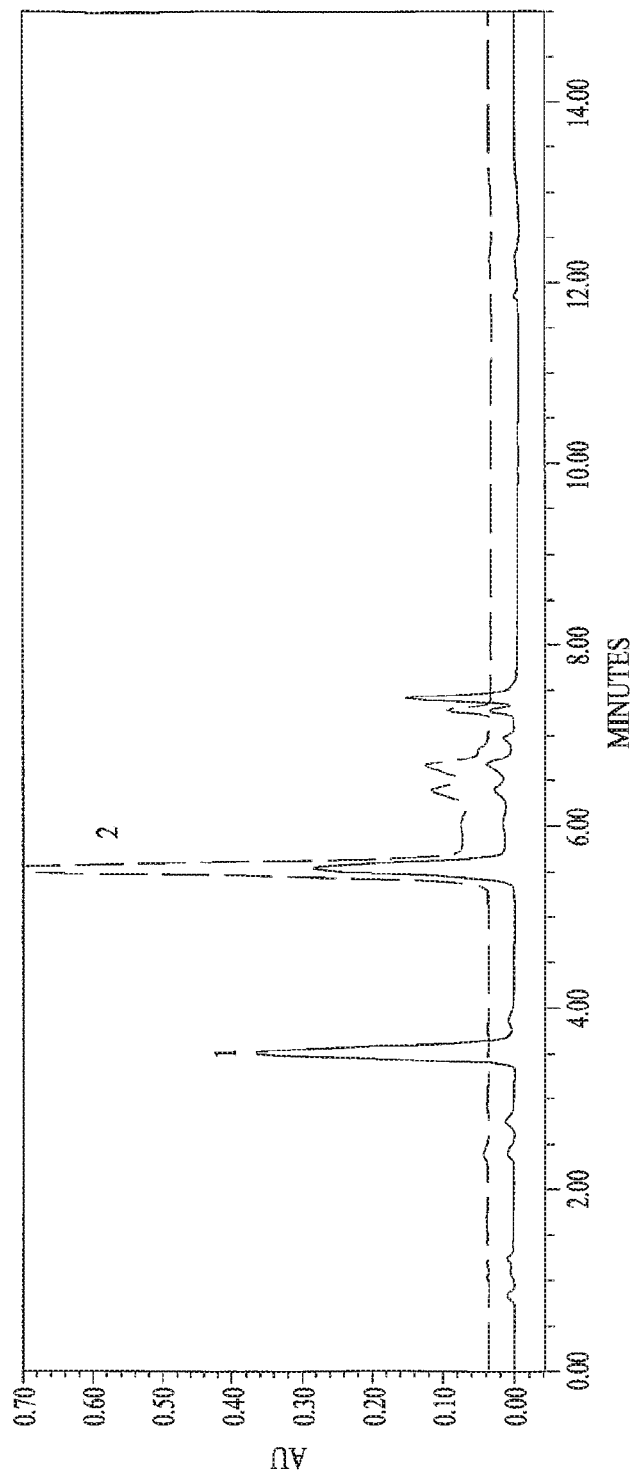
FIG. 4A-4B shows HPLC separation of assay components where the assay was for feruloyl-CoA:monolignol transferase (FMT) activity using feruloyl-CoA and p-coumaryl alcohol as substrates. The UV 340 trace is the dashed line while the UV 280 trace is the solid line.
Figure 4B:
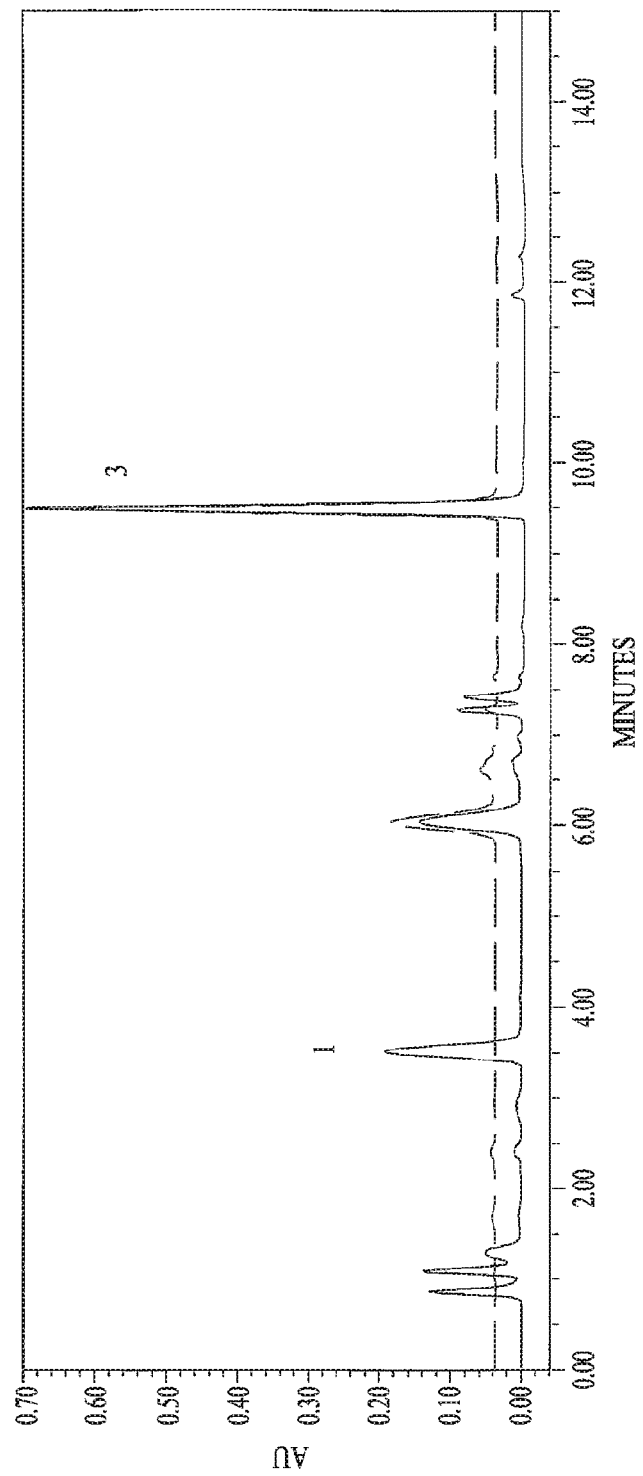
Figure 5A:
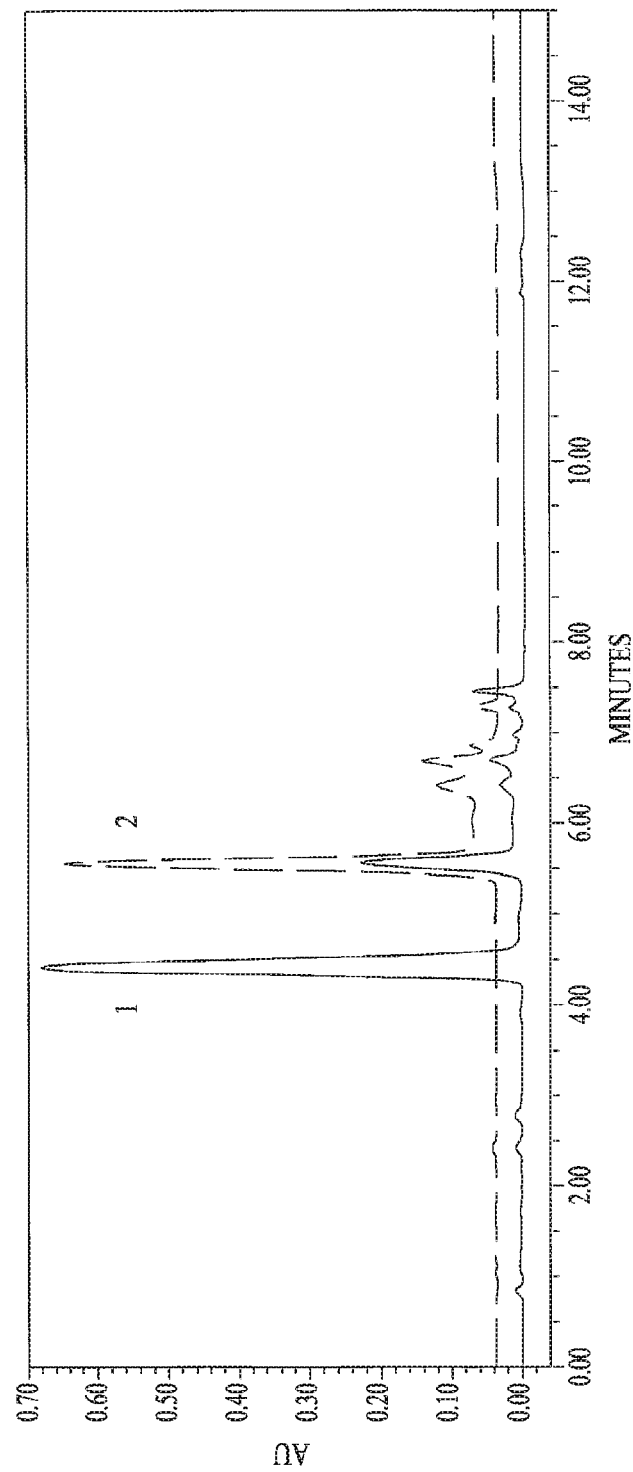
FIG. 5A-5B shows HPLC separation of assay components where the assay was for feruloyl-CoA:monolignol transferase (FMT) activity using sinapyl alcohol and feruloyl-CoA as substrates. The UV 340 trace is the dashed line while the UV 280 trace is the solid line.
Figure 5B:
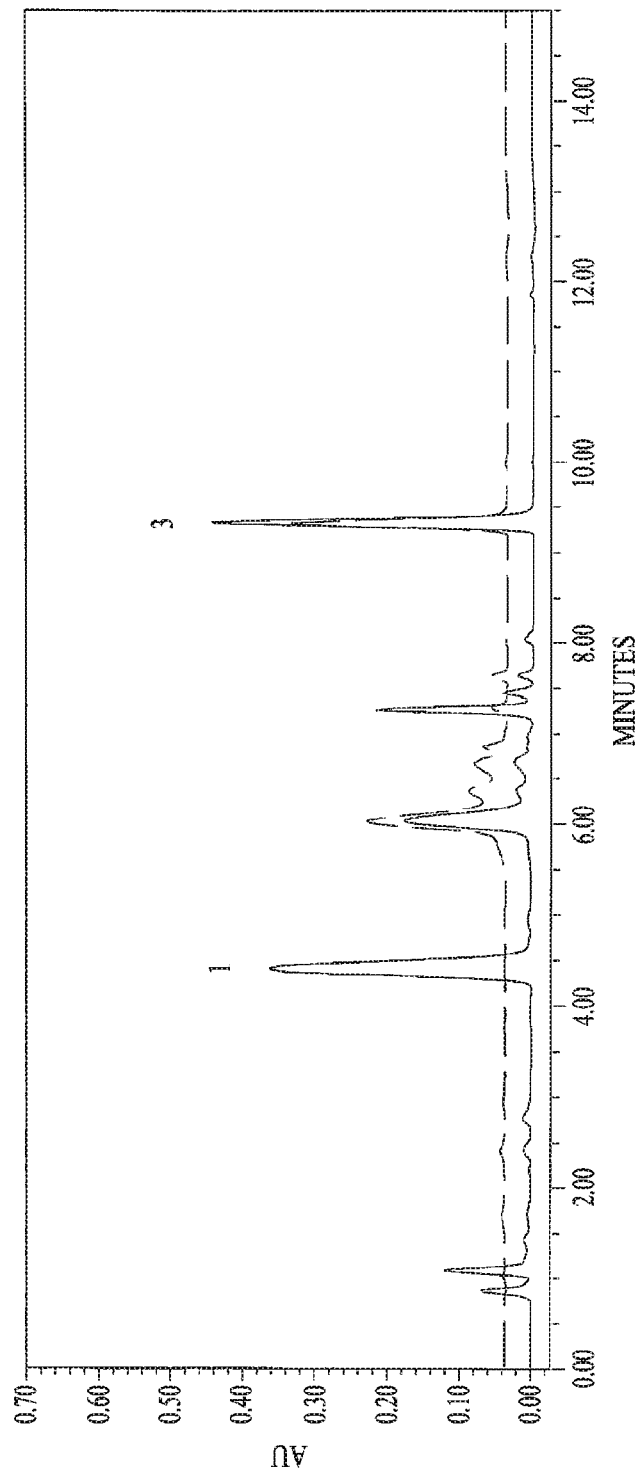
Figure 6A:
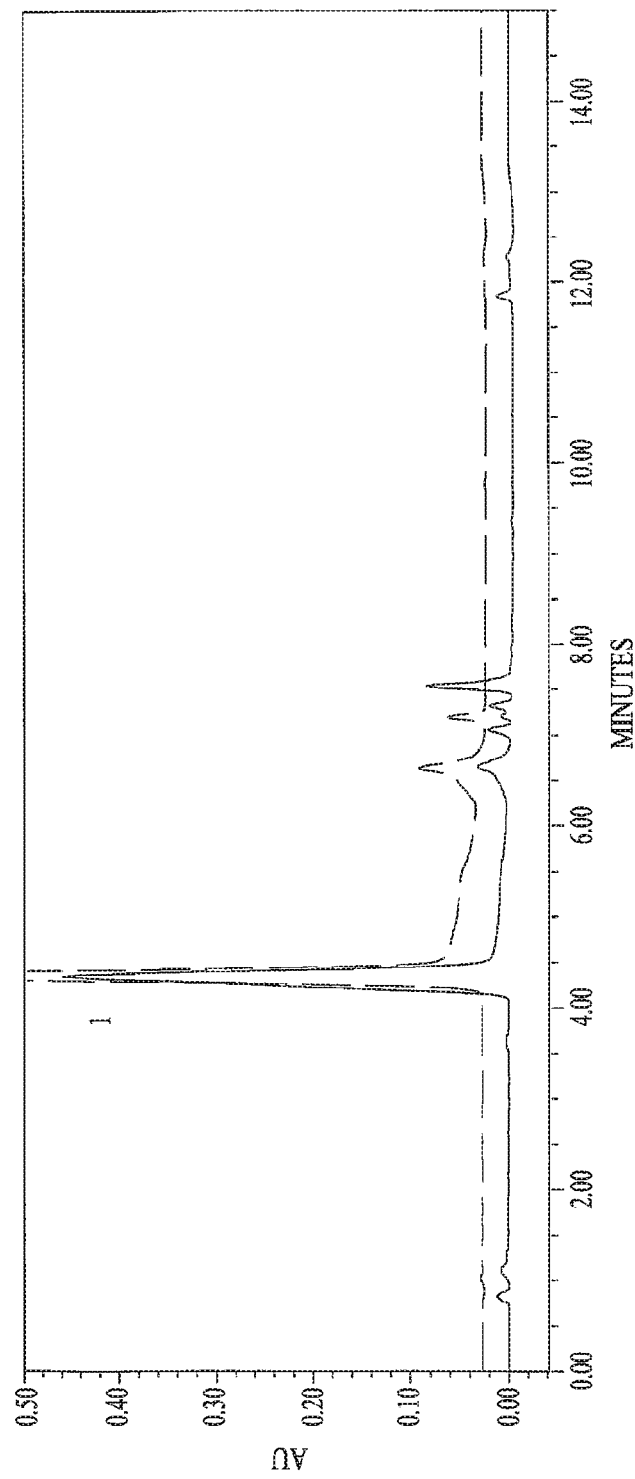
FIG. 6A-6B shows HPLC separation of assay components where the assay was for feruloyl-CoA:monolignol transferase (FMT) activity using coniferyl alcohol and p-coumaroyl-CoA as substrates. The UV 340 trace is the dashed line while the UV 280 trace is the solid line.
Figure 6B:
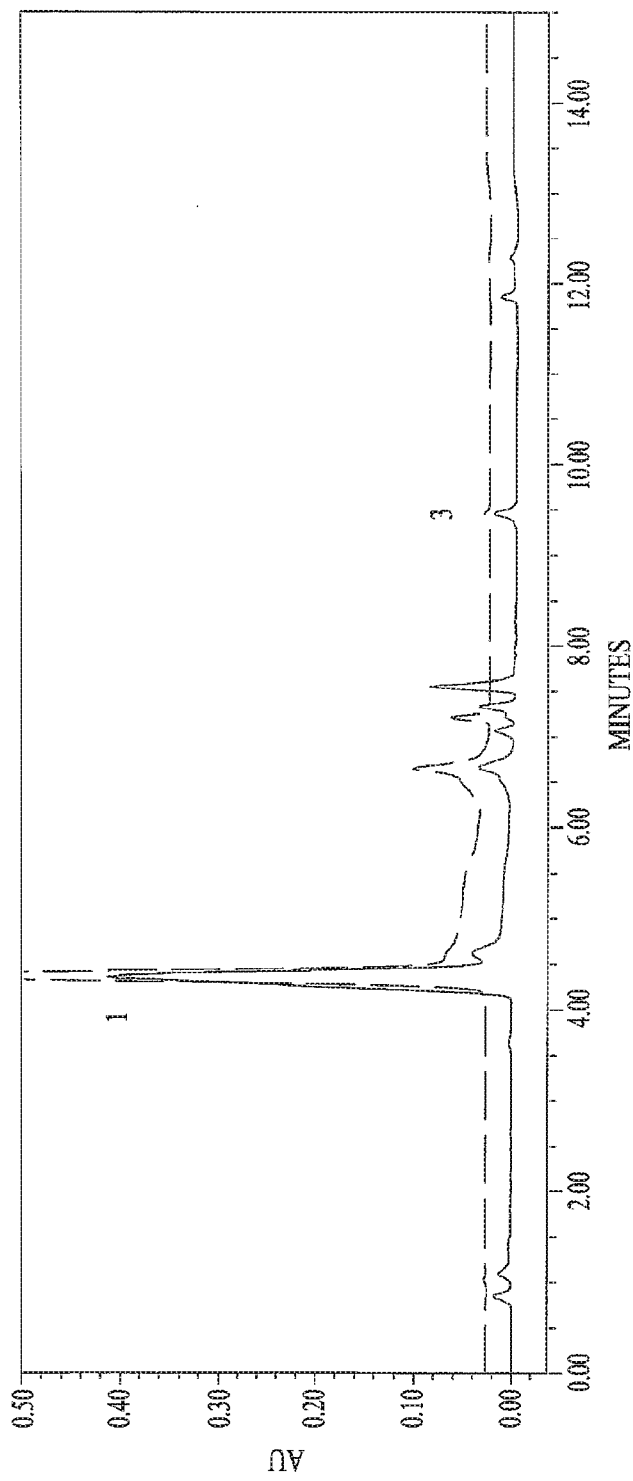
Figure 7A:
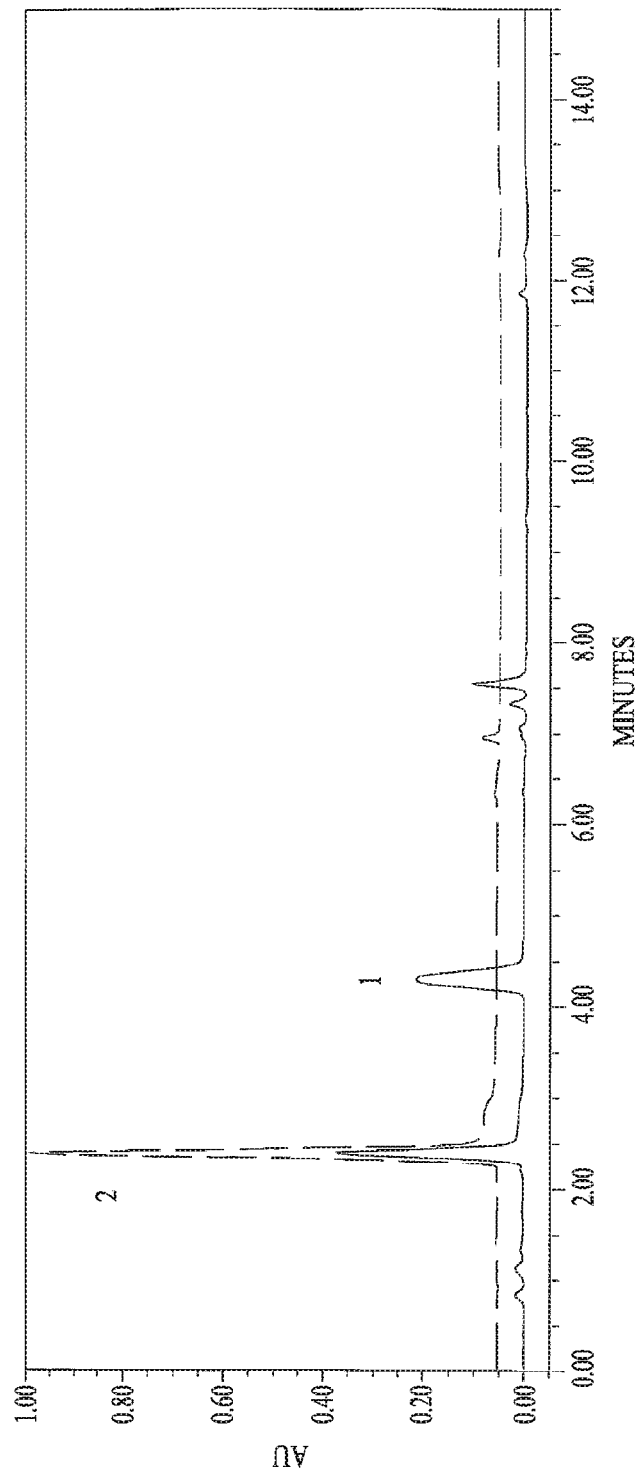

This partial purified product was analyzed by NMR. The identity of the product as CAFA was confirmed by $^1$H-NMR (FIG. 3). The enzyme was tested with p-coumaryl alcohol (FIG. 4) and sinapyl alcohol (FIG. 5) in addition to coniferyl alcohol (FIG. 2). The enzyme is active with all three monolignols, i.e., p-coumaryl alcohol, coniferyl alcohol and sinapyl alcohol. The enzyme was tested with p-coumaroyl-CoA (FIG. 6) and caffeoyl-CoA (FIG. 7) as well as feruloyl-CoA (FIG. 2). The enzyme has a strong preference for feruloyl-CoA as can be seen by comparison of FIGS. 2, 6 and 7. In FIGS. 6 and 7, very little product is produced from p-coumaroyl-CoA and caffeoyl-CoA substrates. However, substantial product is formed when feruloyl-CoA is used instead (FIG. 2).

Figure 8:
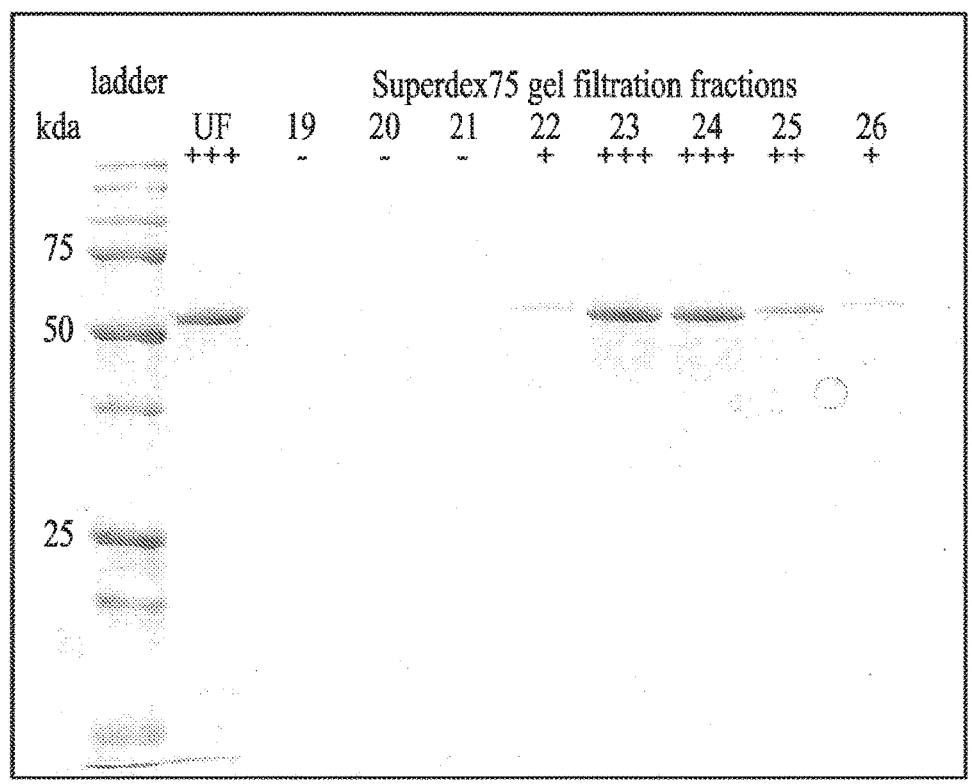
FIG. 8 illustrates SDS-PAGE analysis of size exclusion chromatography fractions from IMAC-purified feruloyl-CoA:monolignol transferase. The term UF is an abbreviations for unfractionated purified feruloyl-CoA:monolignol transferase. The numbers 19 through 26 represent Superdex75 gel filtration fractions. The symbol (−) identifies fractions with no feruloyl-CoA:monolignol transferase activity while the symbols (+), (++) and (+++) mark fractions with progressively increased activity.

The IMAC purified FMT had a few lower molecular weight proteins as shown in FIG. 8. These lower molecular proteins are likely proteolytic fragments of FMT as determined by analysis of tryptic digests of these bands by mass spectrometry. To ensure that the major band was responsible for the activity. FMT was further purified using size-exclusion chromatography. The FMT activity elutes coincident with the major protein band (FIG. 8).

Example 3: Analysis of Transgenic Poplar Containing the FMT Sequence

This Example illustrates the expression and enzymatic activity observed in poplar trees that were genetically modified to express the *Angelica sinensis* feruloyl-CoA:monolignol transferase nucleic acids described herein.

Methods

Hybrid poplar (*Populus alba×grandidentata*) was transformed using *Agrobacterium tumefaciens* EHA105 employing a common leaf disk inoculation. Two constructs were created to drive the expression of FMT in poplar: 1) 35S::YFP-FMT (cauliflower mosaic virus ubiquitous 35S promoter with an N-terminal tagged Yellow Fluorescent Protein), and 2) CesA8::YFP-FMT (poplar xylem-specific secondary cell wall specific cellulose synthase 8 promoter with an N-terminal tagged Yellow Fluorescent Protein). The binary plasmids were inserted into EHA105 using the freeze-thaw technique, and incubated overnight in liquid Woody Plant Media (WPM) supplemented with 100 µM acetosyringone. Leaf disks were cut and co-cultured with EHA105 for one hour at room temperature, blotted dry and plated abaxailly onto WPM supplemented with 0.1 µM each α-naphthalene acetic acid (NAA), 6-benzylaminopurine (BA), and thiadiazuron (TDZ) and solidified with 3% (w/v) agar and 1.1% (w/v) phytagel (WPM 0.1/0.1/0.1). After three days the discs were transferred to WPM 0.1/0.1/0.1 supplemented with carbenicillin disodium (500 mg L$^{-1}$) and cefotaxime sodium salt (250 mg L$^{-1}$). Following three additional days, the discs were transferred to WPM 0.1/0.1/0.1 containing carbenicillin, cefotaxime and hygromycin (25 mg L$^{-1}$). After five weeks, shoots and callus material were transferred to WPM with agar and phytagel, 0.01 µM BA, carbenicillin, cefotaxime and hygromycin. Once individual shoots were visible, plantlets were transferred to solidified WPM with 0.01 µM NAA and carbenicillin, cefotaxime and hygromycin to induce rooting. After two consecutive five-week periods on this media, shoot tips were isolated to solidified antibiotic-free WPM with 0.01 µM NAA.

Plants were confirmed as transgenic by PCR screening of genomic DNA employing gene specific oligonucleotides. All shoot cultures, including transgenic and non-transformed wild-type lines, were maintained on solid WPM with 0.01 µM NAA in GA-7 vessels at 22° C. under a 16-hour photoperiod with an average photon flux of 50 µmol m$^{-2}$ s$^{-1}$ until out-planting to the greenhouse. Plants were then transferred to soil and grown under supplemental lights (@300 W m$^2$) on flood tables and watered with fertigated water daily in a greenhouse.

Purification of YFP-FMT was via GFPtrap_A (Chromotek) following the manufactures guidelines. Briefly, leaves from transgenic 1-year poplar trees were ground to a powder in liquid nitrogen and 250 mg powder of each ground leaf sample was separately suspended in 300 µl 100 mM sodium phosphate pH 6. An aliquot of 5 ul was added to the FMT enzyme assay described in the foregoing Examples. After 45 minutes of incubation, the reaction was stopped with 100 mM hydrochloric acid, and the products were solubilized with the addition of methanol to a concentration of 50%. The protein and insoluble materials were removed by filtration through an Amicon Ultracel 10K membrane filter (Millipore). Control reactions were also completed using a protein extract from wild type hybrid poplar, as well as the standard no enzyme control. These samples were analyzed by western blot and the UPLC method described in the Examples above. Formation of coniferyl ferulate was also detected by comparison of the UPLC traces of leaf extracts with authentic coniferyl ferulate.

Results

Figure 10A:
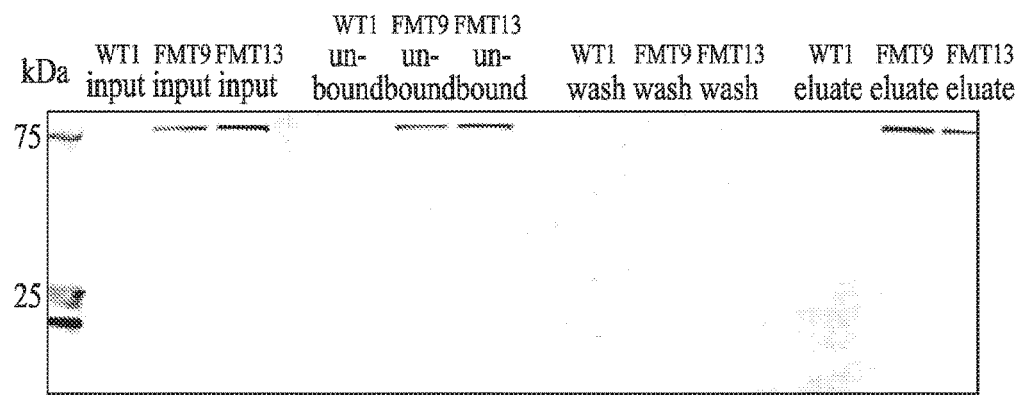
FIGS. 10A-10B illustrate that transgenic Poplar tree leaves express an enzymatically active *Angelica sinensis* feruloyl-CoA:monolignol transferase. The Poplar trees were genetically modified using standard procedures to incorporate the *Angelica sinensis* FMT nucleic acids described herein.
Figure 10B:
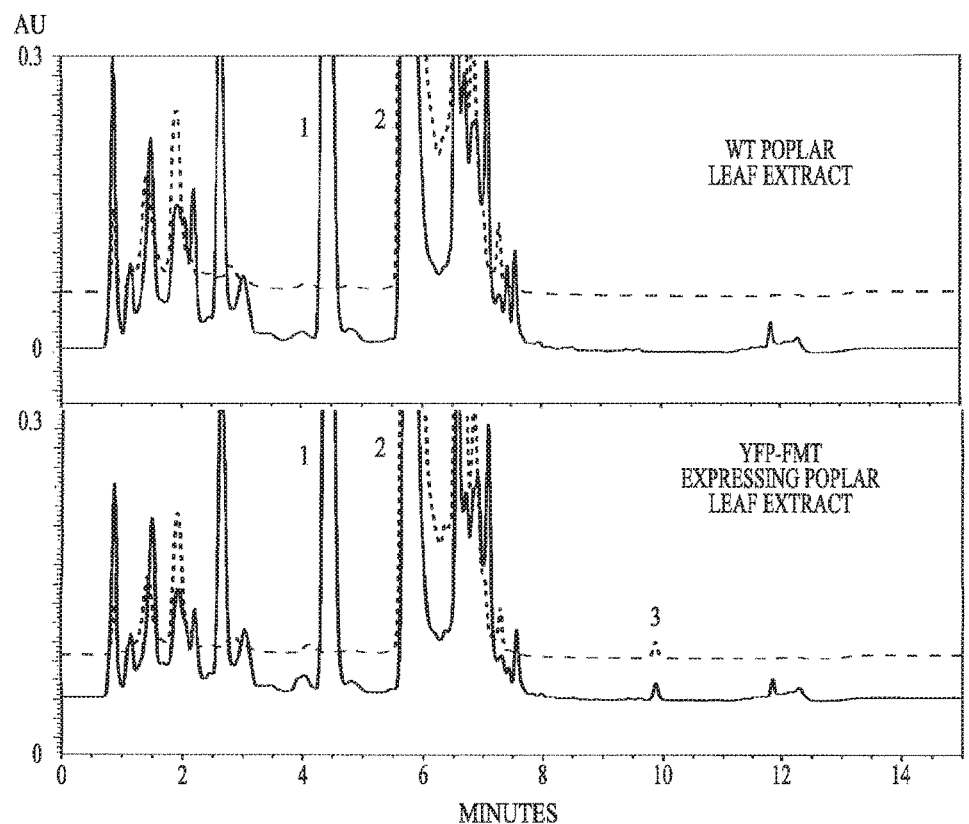

As shown in FIG. 10, FMT activity was identified in extracts from transgenic poplar lines containing the *Angelica sinensis* FMT by observing a product peak at the same retention time as the authentic standard (FIG. 10B). No such peak was observed for wild type popular leaf extracts or in the no enzyme control. Similarly, FMT protein expression was detected by western blot analysis only in leaves from poplar trees that had been genetically modified to express the *Angelica sinensis* FMT (FIG. 10A).

Example 4: Analysis of Transgenic *Arabidopsis* Containing the FMT Sequence

This Example illustrates that other plant species can readily be transformed with the *Angelica sinensis* feruloyl-CoA:monolignol transferase nucleic acids described herein to express an enzymatically active FMT.

Methods:

*Arabidopsis* were transformed by standard procedures with the *Angelica sinensis* feruloyl-CoA:monolignol transferase nucleic acids described herein. As a control some samples of *Arabidopsis* were transformed with an empty vector that did not contain the *Angelica sinensis* FMT. FMT expression was detected by Reverse Transcriptase PCR of protein isolated from the transgenic *Arabidopsis* leaves. Enzymatic activity by the expressed FMT was detected using the assay described in Example 1.

Results

Figure 11A:
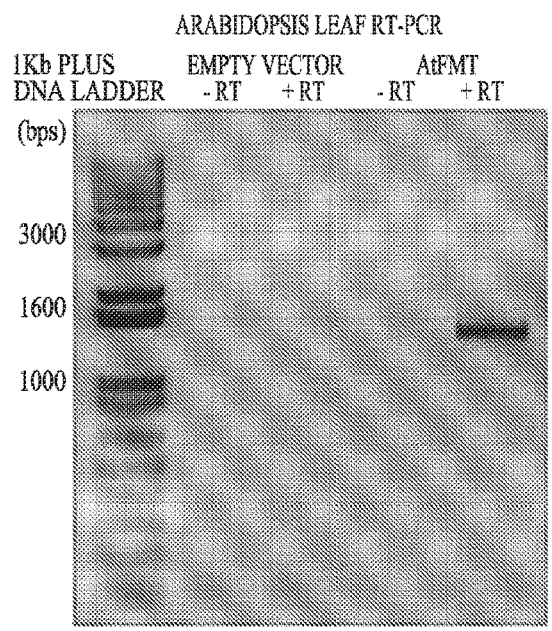
FIGS. 11A-11B illustrate that transgenic *Arabidopsis* express an enzymatically active *Angelica sinensis* feruloyl-CoA:monolignol transferase. FMT expression is demonstrated by Reverse Transcriptase PCR in *Arabidopsis* leaf. FMT enzymatic activity is demonstrated within the *Arabidopsis* stem.

As illustrated in FIG. 11, the transgenic *Arabidopsis* plants express an enzymatically active *Angelica sinensis* feruloyl-CoA:monolignol transferase. FIG. 11A shows the products of Reverse Transcriptase PCR amplification of transcripts from *Arabidopsis* leaves transformed with empty vector or with a vector expressing the FMT transcript. As shown, FMT transcripts were detected only when reverse transcriptase was added (+RT) to the PCR reaction mixture, and not when reverse transcriptase was absent (−RT) from the PCR reaction mixture. A PCR product of the expected size for the FMT enzyme (1326 base pairs) was visible only in the reaction containing total RNA from *Arabidopsis* transformed with the *Angelica sinensis* FMT when the reverse transcriptase is present.

Figure 11B:
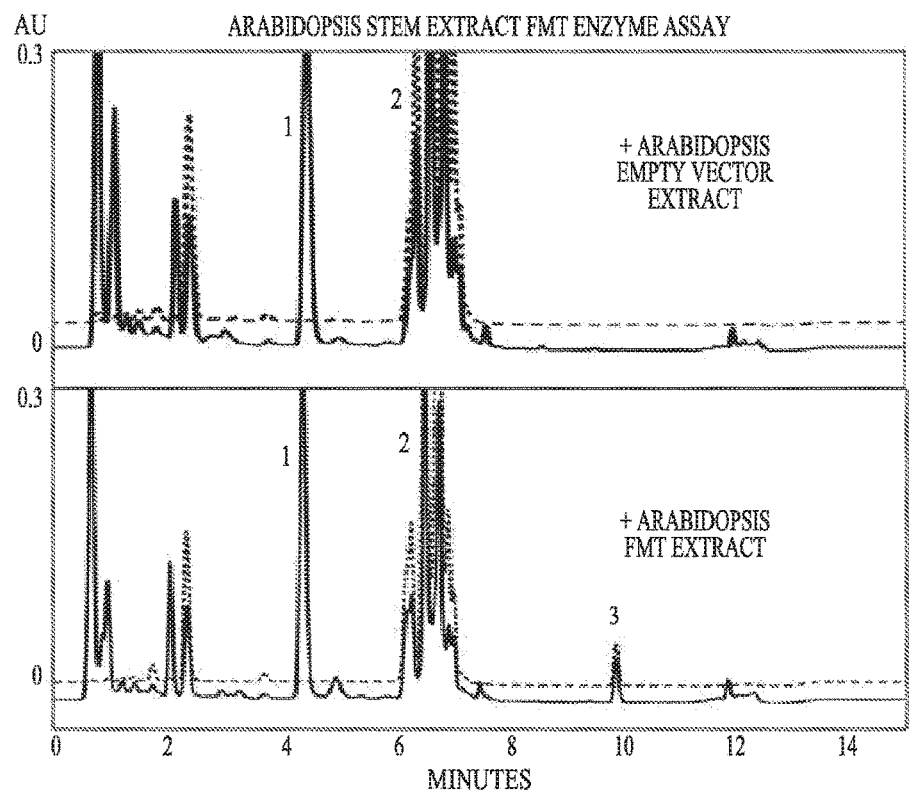

FIG. 11B shows representative UPLC traces illustrating FMT activity in ground stems from *Arabidopsis* transformed with the FMT from *Angelica sinensis* (see, bottom panel). The absorbance for each of the substrates, coniferyl alcohol (1) and feruloyl-CoA (2) and for the product, coniferyl ferulate (3), was detected at 280 nm (solid line) and at 340 nm (dotted line). The top panel of FIG. 11B shows the results of control reactions of stems transformed with empty vector (top panel). Coniferyl ferulate (3) is detected only when protein from the transformed *Arabidopsis*-FMT stems was added.

These data indicate that plants can readily be transformed with the *Angelica sinensis* nucleic acids described herein and such transformed plants can readily express an enzymatically active feruloyl-CoA:monolignol transferase that incorporates monolignol ferulates such as coniferyl ferulate into plant tissues.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

Other embodiments are within the following claims.

What is claimed:

1. An expression cassette comprising a promoter operably linked to a nucleic acid encoding a feruloyl-CoA:monolignol transferase polypeptide with at least 95% sequence identity to SEQ ID NO:2.

2. The expression cassette of claim 1, wherein the nucleic acid encodes a feruloyl-CoA:monolignol transferase that can catalyze the synthesis of monolignol ferulate(s) from monolignol(s) and feruloyl-CoA.

3. The expression cassette of claim 1, wherein the promoter is a promoter functional during plant development or growth.

4. The expression cassette of claim 1, wherein the promoter is a xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene or actin promoter from rice.

5. The expression cassette of claim 1, where any amino acid differences in the polypeptide relative to SEQ ID NO:2 are conservative amino acid substitutions.

6. A plant cell comprising an expression cassette comprising a promoter operably linked to a nucleic acid encoding a feruloyl-CoA:monolignol transferase polypeptide with at least 95% sequence identity to SEQ ID NO:2.

7. The plant cell of claim 6, wherein the plant cell is a monocot cell, maize cell, grass cell, or softwood cell.

8. The plant cell of claim 6, wherein the plant cell is a dicot cell, a hardwood cell, or a eucalyptus plant cell.

9. The plant cell of claim 6, where any amino acid differences in the polypeptide relative to SEQ ID NO:2 are conservative amino acid substitutions.

10. A plant or plant seed comprising an expression cassette comprising a heterologous promoter operably linked to a nucleic acid encoding a feruloyl-CoA:monolignol transferase polypeptide with at least 95% sequence identity to SEQ ID NO:2.

11. The plant or plant seed of claim 10, wherein the plant or plant seed is a monocot, grass, maize, gymnosperm, or softwood plant or plant seed.

12. The plant or plant seed of claim 10, wherein the plant or plant seed is a dicot, hardwood, or eucalyptus plant or plant seed.

13. The plant or plant seed of claim 10, wherein the percent of monolignol ferulates in lignin of the plant or plant grown from the seed is increased at least 1% relative to a corresponding untransformed plant.

14. The plant or plant seed of claim 10, wherein the percent of monolignol ferulates in the lignin of the plant or plant grown from the seed is increased by at least 2-5% relative to a corresponding untransformed plant.

15. The plant or plant seed of claim 10, wherein lignin in the plant or a plant grown from the seed comprises about 1-30% monolignol ferulates.

16. The plant or plant seed of claim 10, wherein the plant is a fertile plant.

17. The plant or plant seed of claim 10, where any amino acid differences in the polypeptide relative to SEQ ID NO:2 are conservative amino acid substitutions.

18. A product comprising tissue from the plant or plant seed of claim 10.

19. A method for incorporating monolignol ferulates into lignin of a plant, comprising:
    a) stably transforming plant cells with an expression cassette comprising a promoter operably linked to a nucleic acid encoding a feruloyl-CoA:monolignol transferase polypeptide with at least 95% sequence identity to SEQ ID NO:2 to generate transformed plant cells;
    b) regenerating the transformed plant cells into at least one transgenic plant, wherein the feruloyl-CoA:monolignol transferase is expressed in at least one transgenic plant, to thereby incorporate monolignol ferulates into the lignin of the transgenic plant.

20. The method of claim 19, wherein the transgenic plant is fertile.

21. The method of claim 19, further comprising recovering transgenic seeds from the transgenic plant, wherein the transgenic seeds comprise the nucleic acid encoding a feruloyl-CoA:monolignol transferase.

22. The method of claim 19, wherein the plant is a monocot, a grass, a maize, gymnosperm plant, or a softwood plant.

23. The method of claim 19, wherein the plant is a dicot, hardwood, or *eucalyptus* plant.

24. The method of claim 19, wherein the lignin in the plant comprises about 1-30% monolignol ferulate.

25. The method of claim 19, further comprising breeding the transgenic plant to yield a progeny plant that has an increase in the percentage of monolignol ferulates in the lignin of the progeny plant relative to a corresponding untransformed plant, and wherein said progeny plant comprises said expression cassette.

26. The method of claim 19, further comprising breeding the fertile transgenic plant to yield a progeny plant that has an increase in the percentage of monolignol ferulates in the lignin of the progeny plant as a dominant trait while still maintaining functional agronomic characteristics relative to a corresponding untransformed plant, and wherein said progeny plant comprises said expression cassette.

27. The method of claim 19, where any amino acid differences in the polypeptide are conservative amino acid substitutions.

28. A method of making a product from a transgenic plant comprising:
    (a) providing a transgenic plant that includes an expression cassette comprising a promoter operably linked to a nucleic acid encoding a feruloyl-CoA:monolignol transferase polypeptide with at least 95% sequence identity to SEQ ID NO:2; and
    (b) processing the transgenic plant's tissues under conditions sufficient to digest the lignin; and
    thereby generating the product from the transgenic plant, wherein the transgenic plant's tissues comprise lignin having an increased percent of monolignol ferulates relative to a corresponding untransformed plant.

29. The method of claim 28, wherein the conditions sufficient to digest the lignin comprise conditions sufficient to cleave ester bonds within monolignol ferulate containing lignin.

30. The method of claim 28, wherein the conditions sufficient to digest the lignin comprise mildly alkaline conditions.

31. The method of claim 28, wherein the conditions sufficient to digest the lignin comprise contacting the transgenic plant's tissues with ammonia for a time and a temperature sufficient to cleave ester bonds within monolignol ferulate-containing lignin.

32. The method of claim 28, wherein the conditions sufficient to digest the lignin would not cleave substantially any of the ether and carbon-carbon bonds in lignin from a corresponding plant that does not contain the isolated nucleic acid encoding the feruloyl-CoA:monolignol transferase.

* * * * *

UNITED STATES PATENT AND TRADEMARK OFFICE
CERTIFICATE OF CORRECTION

PATENT NO. : 10,047,113 B2
APPLICATION NO. : 15/237331
DATED : August 14, 2018
INVENTOR(S) : Wilkerson et al.

Page 1 of 1

It is certified that error appears in the above-identified patent and that said Letters Patent is hereby corrected as shown below:

On the Title Page

Item (54) and in the Specification, Column 1, Line 1, "Title", delete "FERULOYL-COA:MONOLIGNOL" and insert --FERULOYL-CoA:MONOLIGNOL-- therefor On page 4, in Column 2, under "Other Publications", Line 57, delete "Acide" and insert --Acid-- therefor On page 5, in Column 1, under "Other Publications", Line 7, delete "Frerulate" and insert --Ferulate-- therefor On page 5, in Column 1, under "Other Publications", Line 20, delete "Invloved" and insert --Involved-- therefor On page 5, in Column 1, under "Other Publications", Line 21, delete "REgulation" and insert --Regulation-- therefor On page 5, in Column 1, under "Other Publications", Line 31, delete "proteiin" and insert --protein-- therefor On page 5, in Column 1, under "Other Publications", Line 51, delete ""Austrailian" and insert --"Australian-- therefor On page 5, in Column 1, under "Other Publications", Line 53, delete ""Austrailian" and insert --"Australian-- therefor Signed and Sealed this
Twenty-eighth Day of May, 2019

Andrei Iancu
*Director of the United States Patent and Trademark Office*